US012723277B2

(12) United States Patent
Pel et al.

(10) Patent No.: US 12,723,277 B2
(45) Date of Patent: Sep. 1, 2026

(54) LINKED TARGET CAPTURE

(71) Applicant: NCAN Genomics, Inc., Vancouver (CA)

(72) Inventors: Joel Pel, Vancouver (CA); Andrea Marziali, North Vancouver (CA)

(73) Assignee: NCAN Genomics, Inc., Vancouver (CA)

( * ) Notice: Subject to any disclaimer, the term of this patent is extended or adjusted under 35 U.S.C. 154(b) by 985 days.

(21) Appl. No.: 17/614,746

(22) PCT Filed: Jun. 10, 2020

(86) PCT No.: PCT/US2020/036910

§ 371 (c)(1),
(2) Date: Nov. 29, 2021

(87) PCT Pub. No.: WO2020/251968

PCT Pub. Date: Dec. 17, 2020

(65) Prior Publication Data

US 2022/0228206 A1 Jul. 21, 2022

Related U.S. Application Data

(60) Provisional application No. 62/859,486, filed on Jun. 10, 2019.

(51) Int. Cl.

| | |
|---|---|
| ***C12Q 1/6855*** | (2018.01) |
| ***C12N 9/22*** | (2006.01) |
| ***C12N 15/11*** | (2006.01) |
| ***C12Q 1/6806*** | (2018.01) |
| ***C12Q 1/6876*** | (2018.01) |

(52) U.S. Cl.
CPC ............ *C12Q 1/6855* (2013.01); *C12N 9/22* (2013.01); *C12N 15/11* (2013.01); *C12N 15/111* (2013.01); *C12Q 1/6806* (2013.01); *C12Q 1/6876* (2013.01); *C12N 2310/20* (2017.05); *C12N 2310/3231* (2013.01); *C12N 2800/80* (2013.01)

(58) Field of Classification Search
CPC .. C12Q 1/6855; C12Q 1/6806; C12Q 1/6876; C12Q 2525/155; C12Q 2535/122; C12Q 2563/179; C12N 9/22; C12N 15/11; C12N 15/111; C12N 2310/20; C12N 2310/3231; C12N 2800/80
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 5,122,450 | A | 6/1992 | Feizi et al. |
| 5,604,097 | A | 2/1997 | Brenner |
| 5,636,400 | A | 6/1997 | Young |
| 5,695,934 | A | 12/1997 | Brenner |
| 5,846,719 | A | 12/1998 | Brenner et al. |
| 5,863,722 | A | 1/1999 | Brenner |
| 6,138,077 | A | 10/2000 | Brenner |
| 6,150,516 | A | 11/2000 | Brenner et al. |
| 6,172,214 | B1 | 1/2001 | Brenner |
| 6,172,218 | B1 | 1/2001 | Brenner |
| 6,210,891 | B1 | 4/2001 | Nyren et al. |
| 6,235,475 | B1 | 5/2001 | Brenner et al. |
| 6,235,501 | B1 | 5/2001 | Gautsch et al. |
| 6,258,568 | B1 | 7/2001 | Nyren |
| 6,274,320 | B1 | 8/2001 | Rothberg et al. |
| 6,306,597 | B1 | 10/2001 | Macevicz |
| 6,352,828 | B1 | 3/2002 | Brenner |
| 6,719,449 | B1 | 4/2004 | Laugham, Jr. et al. |
| 6,818,395 | B1 | 11/2004 | Quake et al. |
| 6,828,100 | B1 | 12/2004 | Ronaghi |
| 6,833,246 | B2 | 12/2004 | Balasubramanian |
| 6,911,345 | B2 | 6/2005 | Quake et al. |
| 6,948,843 | B2 | 9/2005 | Laugham, Jr. et al. |
| 7,041,481 | B2 | 5/2006 | Anderson et al. |
| 7,057,026 | B2 | 6/2006 | Barnes et al. |
| 7,169,560 | B2 | 1/2007 | Lapidus et al. |
| 7,232,656 | B2 | 6/2007 | Balasubramanian et al. |
| RE39,793 | E | 8/2007 | Brenner |
| 7,282,337 | B1 * | 10/2007 | Harris ................. C12Q 1/6869 435/6.1 |
| 7,393,665 | B2 | 7/2008 | Brenner |
| 7,537,897 | B2 | 5/2009 | Brenner et al. |
| 7,544,473 | B2 | 6/2009 | Brenner |
| 7,598,035 | B2 | 10/2009 | Macevicz |
| 7,708,949 | B2 | 5/2010 | Stone et al. |
| RE41,780 | E | 9/2010 | Anderson et al. |

(Continued)

FOREIGN PATENT DOCUMENTS

| | | |
|---|---|---|
| CA | 3048420 A1 | 6/2018 |
| EP | 2405017 A1 | 1/2012 |

(Continued)

OTHER PUBLICATIONS

Pel et al., Rapid and highly-specific generation of targeted DNA sequencing libraries enabled by linking capture probes with universal primers. PLoS One (2018), 13(12): e0208283, pp. 1—(Year: 2018).*

(Continued)

*Primary Examiner* — Catherine Konopka

(74) *Attorney, Agent, or Firm* — Zachary D. Hyde; Sullivan & Worcester LLP

(57) ABSTRACT

The invention generally relates to using linked target capture probes to evaluate genome editing efficiency and specificity.

15 Claims, 13 Drawing Sheets

Specification includes a Sequence Listing.

(56) References Cited

U.S. PATENT DOCUMENTS

| | | | |
|---|---|---|---|
| 7,835,871 | B2 | 11/2010 | Kain et al. |
| 7,960,120 | B2 | 6/2011 | Rigatti et al. |
| 8,053,192 | B2 | 11/2011 | Bignell et al. |
| 9,404,146 | B2 | 8/2016 | Travers et al. |
| 9,752,188 | B2 | 9/2017 | Schmitt et al. |
| 9,970,054 | B2 | 5/2018 | Otwinowski et al. |
| 2002/0164629 | A1 | 11/2002 | Quake et al. |
| 2003/0194706 | A1 | 10/2003 | Brevnov |
| 2005/0112590 | A1 | 5/2005 | Boom et al. |
| 2006/0024681 | A1 | 2/2006 | Smith et al. |
| 2006/0292611 | A1 | 12/2006 | Berka et al. |
| 2007/0070349 | A1 | 3/2007 | Harris et al. |
| 2007/0114362 | A1 | 5/2007 | Feng et al. |
| 2007/0166705 | A1 | 7/2007 | Milton et al. |
| 2007/0254284 | A1 | 11/2007 | Zhao |
| 2008/0003142 | A1 | 1/2008 | Link et al. |
| 2008/0014589 | A1 | 1/2008 | Link et al. |
| 2008/0081330 | A1 | 4/2008 | Kahvejian |
| 2009/0026082 | A1 | 1/2009 | Rothberg et al. |
| 2009/0118128 | A1 | 5/2009 | Liu et al. |
| 2009/0127589 | A1 | 5/2009 | Rothberg et al. |
| 2009/0191565 | A1 | 7/2009 | Lapidus et al. |
| 2009/0233814 | A1 | 9/2009 | Bashkirov et al. |
| 2010/0009353 | A1 | 1/2010 | Barnes et al. |
| 2010/0035252 | A1 | 2/2010 | Rothberg et al. |
| 2010/0081141 | A1 | 4/2010 | Chen et al. |
| 2010/0111768 | A1 | 5/2010 | Banerjee et al. |
| 2010/0137143 | A1 | 6/2010 | Rothberg et al. |
| 2010/0137163 | A1 | 6/2010 | Link et al. |
| 2010/0172803 | A1 | 7/2010 | Stone et al. |
| 2010/0188073 | A1 | 7/2010 | Rothberg et al. |
| 2010/0196890 | A1 | 8/2010 | Wittwer et al. |
| 2010/0197507 | A1 | 8/2010 | Rothberg et al. |
| 2010/0282617 | A1 | 11/2010 | Rothberg et al. |
| 2010/0300559 | A1 | 12/2010 | Schultz et al. |
| 2010/0300895 | A1 | 12/2010 | Nobile et al. |
| 2010/0301398 | A1 | 12/2010 | Rothberg et al. |
| 2010/0304982 | A1 | 12/2010 | Hinz et al. |
| 2011/0003305 | A1 | 1/2011 | Brentano et al. |
| 2011/0009278 | A1 | 1/2011 | Kain et al. |
| 2011/0207131 | A1* | 8/2011 | Fu ........................ C12Q 1/6823 702/19 |
| 2011/0301042 | A1 | 12/2011 | Steinmann et al. |
| 2013/0122814 | A1 | 5/2013 | Shen et al. |
| 2013/0203123 | A1 | 8/2013 | Nelson et al. |
| 2014/0134610 | A1 | 5/2014 | Pham et al. |
| 2015/0099642 | A1 | 4/2015 | Barany et al. |
| 2015/0105275 | A1 | 4/2015 | Wong et al. |
| 2015/0152492 | A1 | 6/2015 | Brown et al. |
| 2016/0067104 | A1 | 3/2016 | Sarangapani et al. |
| 2016/0122814 | A1 | 5/2016 | Despotovic et al. |
| 2016/0265042 | A1 | 9/2016 | Schroeder et al. |
| 2016/0304950 | A1 | 10/2016 | Joung et al. |
| 2016/0326578 | A1 | 11/2016 | Bielas |
| 2018/0087104 | A1* | 3/2018 | Joung .................. C12Q 1/6855 |
| 2018/0163265 | A1 | 6/2018 | Zhang et al. |
| 2018/0245132 | A1 | 8/2018 | Jiang et al. |
| 2019/0024141 | A1 | 1/2019 | Myllykangas et al. |
| 2019/0106729 | A1 | 4/2019 | Pel et al. |
| 2019/0112654 | A1 | 4/2019 | Pel et al. |
| 2019/0300939 | A1 | 10/2019 | Chen et al. |
| 2020/0040378 | A1 | 2/2020 | Beatty et al. |

FOREIGN PATENT DOCUMENTS

| | | | |
|---|---|---|---|
| WO | 2004/018497 | A2 | 3/2004 |
| WO | 2007/123744 | A2 | 11/2007 |
| WO | 2010/117817 | A2 | 10/2010 |
| WO | 2012/040387 | A1 | 3/2012 |
| WO | 2013/126741 | A1 | 8/2013 |
| WO | 2015104302 | A1 | 7/2015 |
| WO | 2016/149837 | A1 | 9/2016 |
| WO | 2017/168331 | A1 | 10/2017 |
| WO | 2017/168332 | A1 | 10/2017 |
| WO | 2017168329 | A1 | 10/2017 |
| WO | 2018104908 | A2 | 6/2018 |
| WO | 2018108328 | A1 | 6/2018 |
| WO | 2018183607 | A1 | 10/2018 |
| WO | 2020039261 | A1 | 2/2020 |

OTHER PUBLICATIONS

Roberts, 1980, Restriction and modification enzymes and their recognition sequences, Nucleic Acids Res 8(1):r63-r80.

Salk, 2018, Enhancing the accuracy of next-generation sequencing for detecting rare and subclonal mutations, Nature Reviews Genetics, 19(5):269-285.

Sambrook, 1989. Molecular Cloning: A Laboratory Manual. Second Edition. Cold Spring Harbor Laboratory Press, New York, N.Y.

Sargent, 1987, Isolation of differentially expressed genes, Meth Enzym 152:423-432.

Satterfield, 2014, Cooperative Primers, The Journal of Molecular Diagnostics; 16(2) (11 pages).

Schlingman, 2011, A New Method for the Covalent Attachment of DNA to a Surface for Single-Molecule Studies, Colloids and Surfaces B: Biointerfaces 83:91-95.

Schmitt, 2012, Detection of ultra-rare mutations by the next generation sequencing, Proc. Natl. Acad. Sci., 109:14508-14513.

Schmitt, 2012, Detection of ultra-rare mutations by the next-generation sequencing, Proceedings of the National Academy of Sciences, 109(36):14508-14513.

Schmitt, 2013, Detection of ultra-rare mutations by the next-generation sequencing, Proceedings of the National Academy of Sciences, 109(36): Supporting Information, 3 pages.

Schmitt, 2015, Sequencing small genomic targets with high efficiency and extreme accuracy, 12(5):423-426.

Schuette, 1995, Sequence analysis of phosphorothioate oligonucleotides via matrix-assisted laser desorption ionization time-of-flight mass spectrometry, J Pharm Biomed Anal 13:1195-1203.

Smirnov, 1996, Sequencing oligonucleotides by exonuclease digestion and delayed extraction matrix-assisted laser desorption ionization time-of-flight mass spectrometry, Anal Biochem 238:19-25.

Soni, 2007, Progress toward Ultrafast DNA Sequencing Using Solid-State Nanopores, Clinical Chemistry 53:1996-2001.

Thorstenson, 1998, An Automated Hydrodynamic Process for Controlled, Unbiased DNA Shearing, Genome Res 8(8): 848-855.

Tijssen, 1993, Hybridization with Nucleic Acid Probes—Laboratory Techniques in Biochemisrt and Molecular Biology (Parts I and II), Elsevier.

Vold, 1979, Radioimmunoassays for the modified nucleosides N-[9-(β-D-ribofuranosyl)purin-6-ylcarbamoyl]-L-threonine and 2-methylthioadenosine, Nucleic Acid Research, 7(1):193-204.

Williams, 2003, Restriction endonucleases classification, properties, and applications, Mol Biotechnol 23(3):225-43.

Wu, 1998, Sequencing regular and labeled oligonucleotides using enzymatic digestion and ionspray mass spectrometry, Anal Biochem 263:129-138.

Wu, 2001, Improved oligonucleotide sequencing by alkaline phosphatase and exonuclease digestions with mass spectrometry, Anal Biochem 290:347-352.

Yuan, 1981, Structure and mechanism of multifunctional restriction endonucleases, Ann Rev Biochem 50:285-319.

International Search Report mailed Jun. 3, 2020 for International Application No. PCT/IB2020/000027 (4 pages).

Notice of Allowance issued in U.S. Appl. No. 17/417,995, date of mailing: Apr. 18, 2022, 10 pages.

Written Opinion mailed Jun. 3, 2020 for International Application No. PCT/IB2020/000027 (4 pages).

Alazard, 2002, Sequencing of production-scale synthetic oligonucleotides by enriching for coupling failures using matrix-assisted laser desorption/ ionization time-of-flight mass spectrometry, Anal Biochem 301:57-64.

Ansorge, 2009, Next-generation DNA sequencing techniques, New Biotechnology, Elsevier BV, NL, 25(4):195-203.

Barany, 1991, Genetic disease detection and DNA amplification using cloned thermostable ligase, PNAS 88:189-193.

(56) References Cited

OTHER PUBLICATIONS

Barany, 1991, The ligase chain reaction in a PCR World, PCR Methods and Applications, 1(1):5-16.
Bentzley, 1996, Oligonucleotide sequence and composition determined by matrix-assisted laser desorption/ionization, Anal Chem 68:2141-2146.
Bentzley, 1998, Base specificity of oligonucleotide digestion by calf spleen phosphodiesterase with matrix-assisted laser desorption ionization analysis, Anal Biochem 258:31-37.
Bickle, 1993, Biology of DNA Restriction, Microbiol Rev 57(2):434-50.
Boyer, 1971, DNA restriction and modification mechanisms in bacteria, Ann Rev Microbiol 25:153-76.
Braslavsky, 2003, Sequence information can be obtained from single DNA molecules, PNAS, 100:3960-3964.
Brown, 1979, Chemical synthesis and cloning of a tyrosine tRNA gene, Methods Enzymol 68:109-151.
Browne, 2002, Metal ion-catalyzed nucleic acid alkylation and fragmentation, Journal of American Chemical Society, 124(27)7950-62.
Chan, 2011, Natural and engineered nicking endonucleases—from cleavage mechanism to engineering of strand-specificity, Nucl Acids Res 39(1):1-18.
Dappritch, 2016, The Next Generation of Target Capture Technologies—Large DNA Fragment Enrichment and Sequencing Determines Regional Genomic Variation of High Complexity, BMC Genomics, 17:486 (14 pages).
Dieffenbach, 1995, PCR Primer, a Laboratory Manual, Cold Spring Harbor Press, Plainview, NY.
Extended European Search Report issued in European Application No. 20736149.4, date of mailing: Mar. 4, 2022, 11 pages.
Extended European Search Report issued in European Application No. EP17773408.4, date of mailing: Mar. 30, 2019 (13 pages).
Extended European Search Report issued in European Patent Application No. 17877951.8, date of mailing: Sep. 30, 2020, 11 pages.
Faulstich, 1997, A sequencing method for RNA oligonucleotides based on mass spectrometry, Anal Chem 69:4349-4353.
Glover, 1995, Sequencing of oligonucleotides using high performance liquid chromatography and electrospray mass spectrometry, Rapid Com Mass Spec 9:897-901.
Gut, 1995, A procedure for selective DNA alkylation and detection by mass spectrometry, Nucl Acids Res 23 (8):1367-1373.
Harris, 2008, Single-Molecule DNA Sequencing of a Viral Genome, Science, 320:106-109.
International Preliminary Report on Patentability issued in International Patent Application No. PCT/IB2019/000962, date of mailing: Mar. 4, 2021, 7 pages.
International Search Report and Written Opinion issued in International Application No. PCT/IB2017/051776, date of mailing: Jun. 13, 2017 (12 Pages).
International Search Report and Written Opinion issued in International Application No. PCT/IB2017/051778, date of mailing: Jun. 23, 2017 for (12 Pages).
International Search Report and Written Opinion issued in International Application No. PCT/IB2017/051779, date of mailing: Jun. 15, 2017 (14 Pages).
International Search Report and Written Opinion issued in International Application No. PCT/IB2017/057732, date of mailing: Jul. 10, 2018 (7 Pages).
International Search Report and Written Opinion issued in International Application No. PCT/IB2019/000962, date of mailing: Jan. 21, 2020, 9 pages.
International Search Report and Written Opinion issued in International Application No. PCT/US2020/36910, date of mailing: Sep. 18, 2020 (14 pages).
Kirpekar, 1994, Matrix assisted laser desorption/ionization mass spectrometry of enzymatically synthesized RNA up to 150 kDa, Nucl Acids Res 22:3866-3870.
Kolb, 2001, Click Chemistry: Diverse Chemical Function from a Few Good Reactions, Angew Chem Int. Ed. Engl., 40 (1):2004-2021.
Kumar, 2012, PEG-Labeled Nucleotides and Nanopore Detection for Single Molecule DNA Sequencing by Synthesis, Scientific Reports 2, Article 684 (8 pages).
Lee, 1984, Antibodies to Nucleic Acids, Biochemical Education 12(3):98-101.
Lou, 2013, High-Throughput DNA Sequencing Errors are Reduced by Orders fo Magnitude Using Circle Sequencing, PNAS, 110(49):19872-19877.
Maniatis, 1982, Molecular Cloning: A Laboratory Manual, Cold Spring Harbor, NY, pp. 280-281.
Margulies, 2005, Genome sequencing in micro-fabricated high-density picotiter reactors, Nature, 437:376-380.
Maxam, 1977, A new method for Sequencing DNA, Proc. Natl. Acad. Sci., 74:560-564.
Mirkin, 1996, A DNA-based method for rationally assembling nanoparticles into macroscopic materials, Nature, 382:607-609.
Narang, 1979, Improved phosphotriester method for the synthesis of gene fragments, Methods Enzymol, 68:90-98.
Non-Final Office Action issued in U.S. Appl. No. 16/088,717, date of mailing: Jul. 30, 2020 (8 pages).
Non-Final Office Action issued in U.S. Appl. No. 16/088,720, date of mailing: Aug. 5, 2020 (9 pages).
Non-Final Office Action issued in U.S. Appl. No. 16/239,100, date of mailing: Aug. 5, 2020 (9 pages).
Nordhoff, 1993, Ion stability of nucleic acids in infrared matrix-assisted laser desorption/ ionization mass spectrometry, Nucl Acid Res 21(15):3347-57.
Oefner, 1996, Efficient random sub-cloning of DNA sheared in a recirculating point-sink flow system, Nucleic Acids Res 24(20):3879-3886.
Ordahl, 1976, Sheared DNA fragment sizing: comparison of techniques, Nucleic Acids Res 3:2985-2999.
Owens, 1998, Aspects of oligonucleotide and peptide sequencing with MALDI and electrospray mass spectrometry, Bioorg Med Chem 6:1547-1554.
Partial Supplementary European Search Report issued in European Application No. 17877951.8, date of mailing: Jun. 29, 2020 (13 pages).
Pel, 2017, Duplex Proximity Sequencing (Pro-Seq): A Method to Improve DNA Sequencing Accuracy Without the Cost of Molecular Barcoding Redundancy, BioRxiv, Retrieved from <doi:http://dx.doi.org/10.1101/16344> (33 Pages).
Pel, 2018, Abstract 425: Linked Target Capture: Rapid and high-performance NGS target enrichment for clincal sequencing applications, Molecular and Cellular Biology/Genetics (6 pages).
Pieles, 1993, Matrix-assisted laser desorption ionization time-of-flight mass spectrometry: A powerful tool for the mass and sequence analysis of natural and modified oligonucleotides, Nucleic Acids Res 21:3191-3196.
Quail, 2010, DNA: Mechanical Breakage, In Encyclopedia of Life Sciences, John Wiley & Sons Ltd, Chicester (5 pages).
Search Report and Written Opinion dated Sep. 18, 2020, from corresponding international application No. PCT/US2020/036910, and references cited therein.

* cited by examiner

Figure 1:
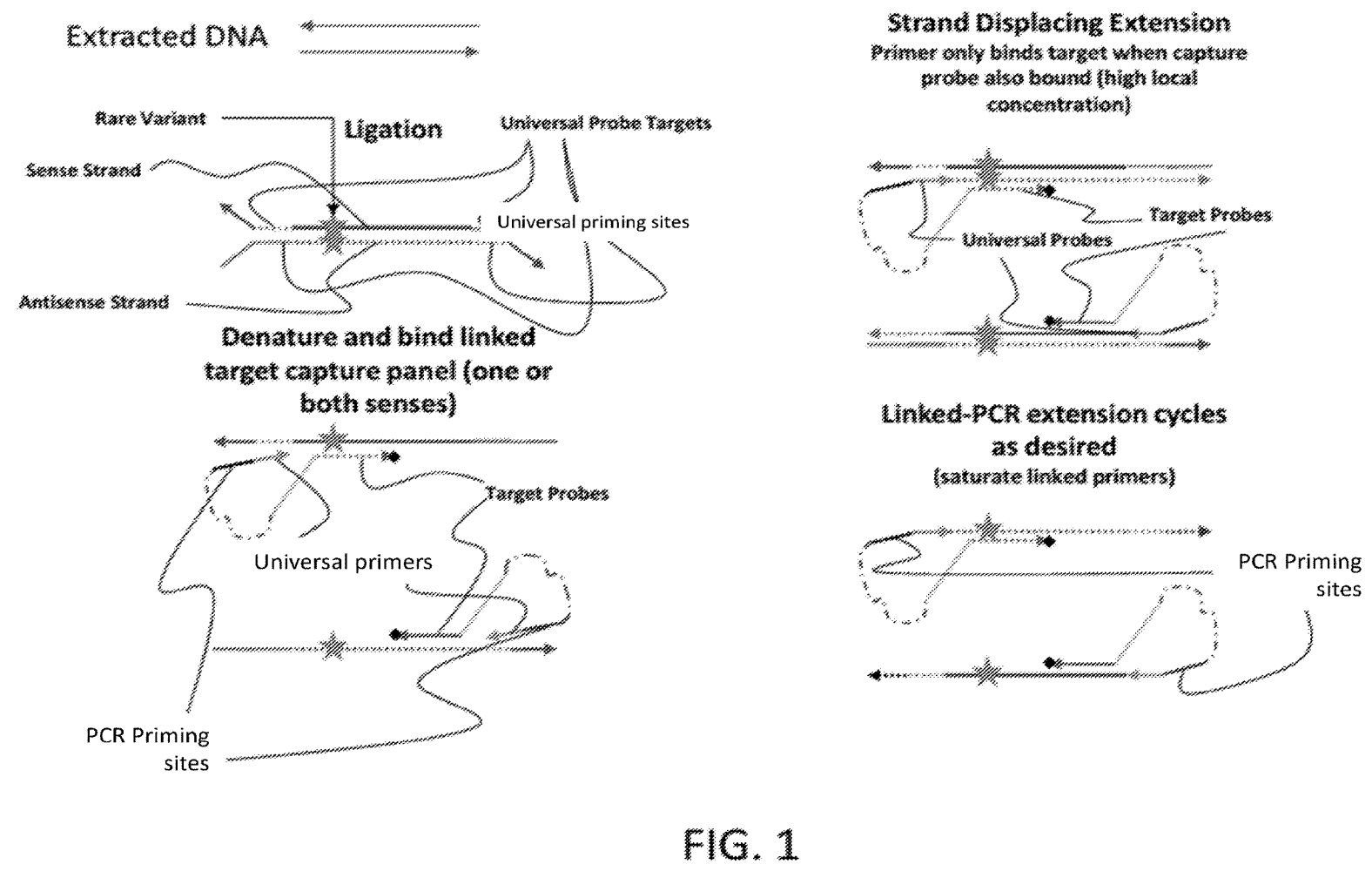

Extracted DNA

Rare Variant

Sense Strand

Antisense Strand

Ligation

Universal Probe Targets

Universal priming sites

Denature and bind linked target capture panel (one or both senses)

Target Probes

Universal primers

PCR Priming sites

Strand Displacing Extension

Primer only binds target when capture probe also bound (high local concentration)

Universal Probes

Target Probes

Linked-PCR extension cycles as desired (saturate linked primers)

PCR Priming sites

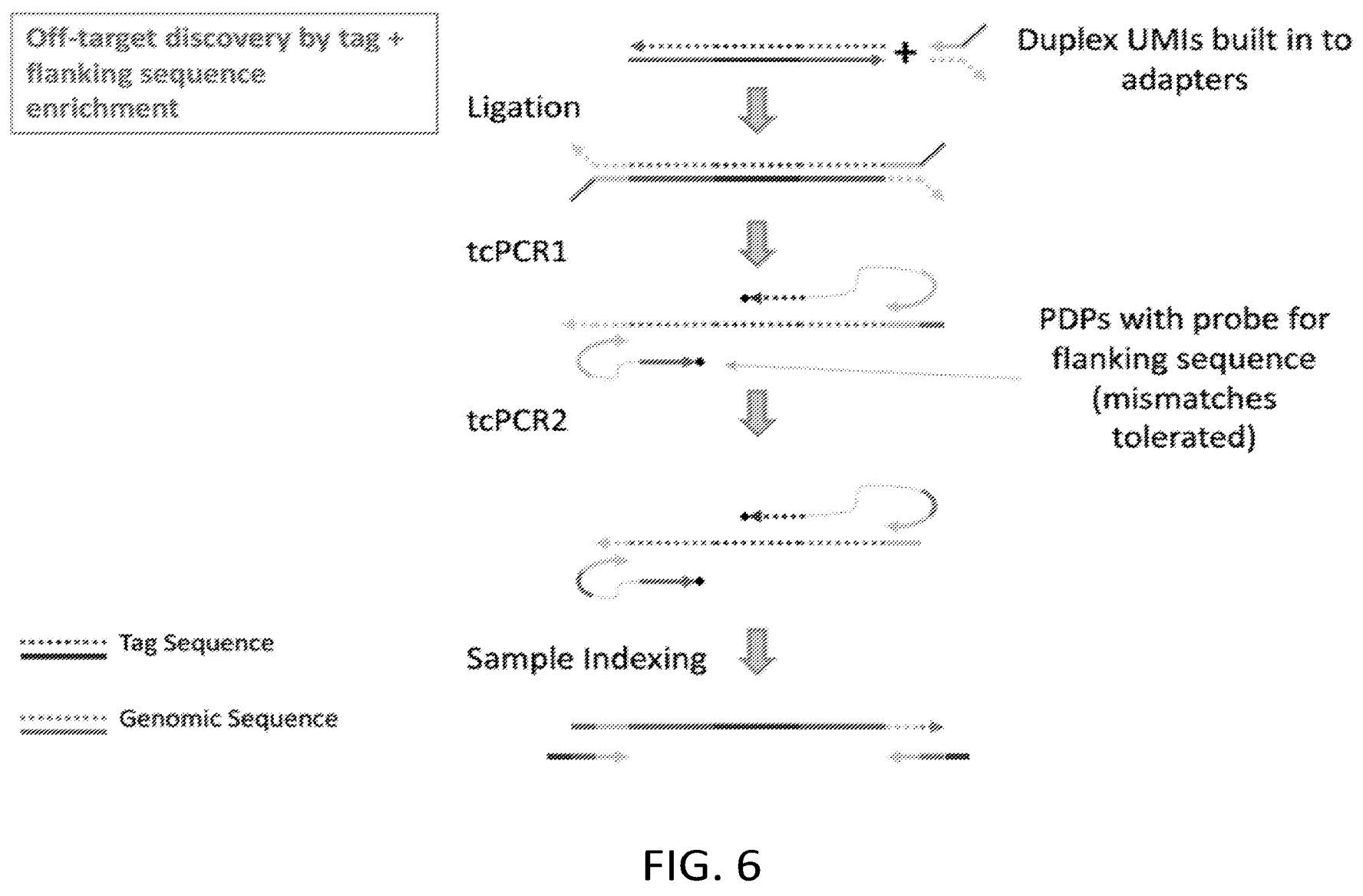

Off-target discovery by tag + flanking sequence enrichment

Duplex UMIs built in to adapters

Ligation tcPCR1

PDPs with probe for flanking sequence (mismatches tolerated)

tcPCR2

Sample Indexing

Tag Sequence

Genomic Sequence

FIG. 6

LINKED TARGET CAPTURE

RELATED APPLICATIONS

This application claims priority to and the benefit of U.S. Provisional Application No. 62/859,486, filed on Jun. 10, 2019, the content of which is hereby incorporated by reference in its entirety.

FIELD OF THE INVENTION

The invention generally relates to capturing, amplifying and sequencing nucleic acids.

BACKGROUND

The advent of more powerful and user-friendly genome editing tools has opened a new world of possibilities in treating genetic disorders, eradicating diseases, improving crop yields/resistances, and other potential advantages of modifying organisms. Systems including clustered regularly interspaced short palindromic repeats (CRISPR) and associated enzymes, meganucleases, transcription activator effector-like nucleases (TALEN), and zinc-finger nucleases allow for the introduction of double-stranded breaks in DNA at specific target sequences which can allow for targeted mutations including the insertion of a desired sequence at the break point.

In order to proof the effectiveness of these tools and promote their acceptance for general use, their efficiency and specificity must be evaluated including assessing integration rates for inserted sequences. Analysis of off-target cleavage and insertion is also important.

SUMMARY

The invention provides methods for evaluating incorporation rates and off-target effects of any of the aforementioned genome editing tools. Inserted double-stranded tag sequences can be enriched for and quantified to assess success rates. The combination of off-target integration monitoring and quantification of on-target integration provides a powerful tool for evaluating genome editing systems.

In certain embodiments, the invention provides methods of linked target capture techniques with probes targeting double-stranded tags inserted using various genome editing tools. Target capture for detecting double stranded breaks can be performed in solution or using droplet-based methods. Linked target capture probes including a universal primer and a target-specific probe are used and reactions occur under conditions that require the target-specific probe to bind in order to permit binding of the universal primer. After integrating a tag sequence using a genome editing method to be analyzed, duplex adapter with a universal priming site can be ligated to the ends of the altered DNA. The target-specific probe can be complimentary to the tag sequence, a genomic DNA sequence flanking the double-stranded break point, or both. This heterogeneously-integrated DNA eNrichment, or HIDN-Seq process described herein allows enrichment of tag sequences or tag and flanking sequences to provide data on integration rates as well as identifying off-target integration, providing a comprehensive assessment of DNA editing performance. Enrichment of tag sequences allows measurement of all integration sites, including undesired off-target sites and uses probes designed against tag sequence only while enrichment of desired integration sites allows measurement of integration rate at a given site and uses probes designed against expected genomic DNA integration sites Because multiple binding steps are required, specificity is improved over traditional single binding target capture techniques. After binding of the linked probe, the bound universal primer is extended using strand displacing polymerase to produce copies of the target strands which can then be amplified using PCR with universal primers. Linked capture probes can be used for both senses of DNA where higher specificity and duplex information are required. Multiple linker types are possible as discussed below. Similar to solution-based target capture methods of the invention provide for droplet based methods that allow a user to perform target capture for DNA integration analysis in droplets, rather than being restricted to multiplexed PCR in droplets.

Barcodes, including duplex unique molecular identifiers (UMI) may be used to tag amplified or enriched sequences such that sense information is retained along with starting molecule information for the double stranded DNA being analyzed. Accordingly, sequencing results can be attributed to individual starting molecules for accurate incorporation rate assessments.

BRIEF DESCRIPTION OF THE FIGURES

FIG. 1 illustrates exemplary methods of linked target capture of duplex nucleic acids.

FIG. 5 shows an exemplary off-target discovery workflow using HIDN-Seq and linked target capture probes specific to the tag sequence.

FIG. 6 shows an exemplary off-target and flanking discovery workflow using HIDN-Seq and linked target capture probes specific to the tag sequence and the breakpoint-flanking genomic DNA region.

DETAILED DESCRIPTION

Figure 2:
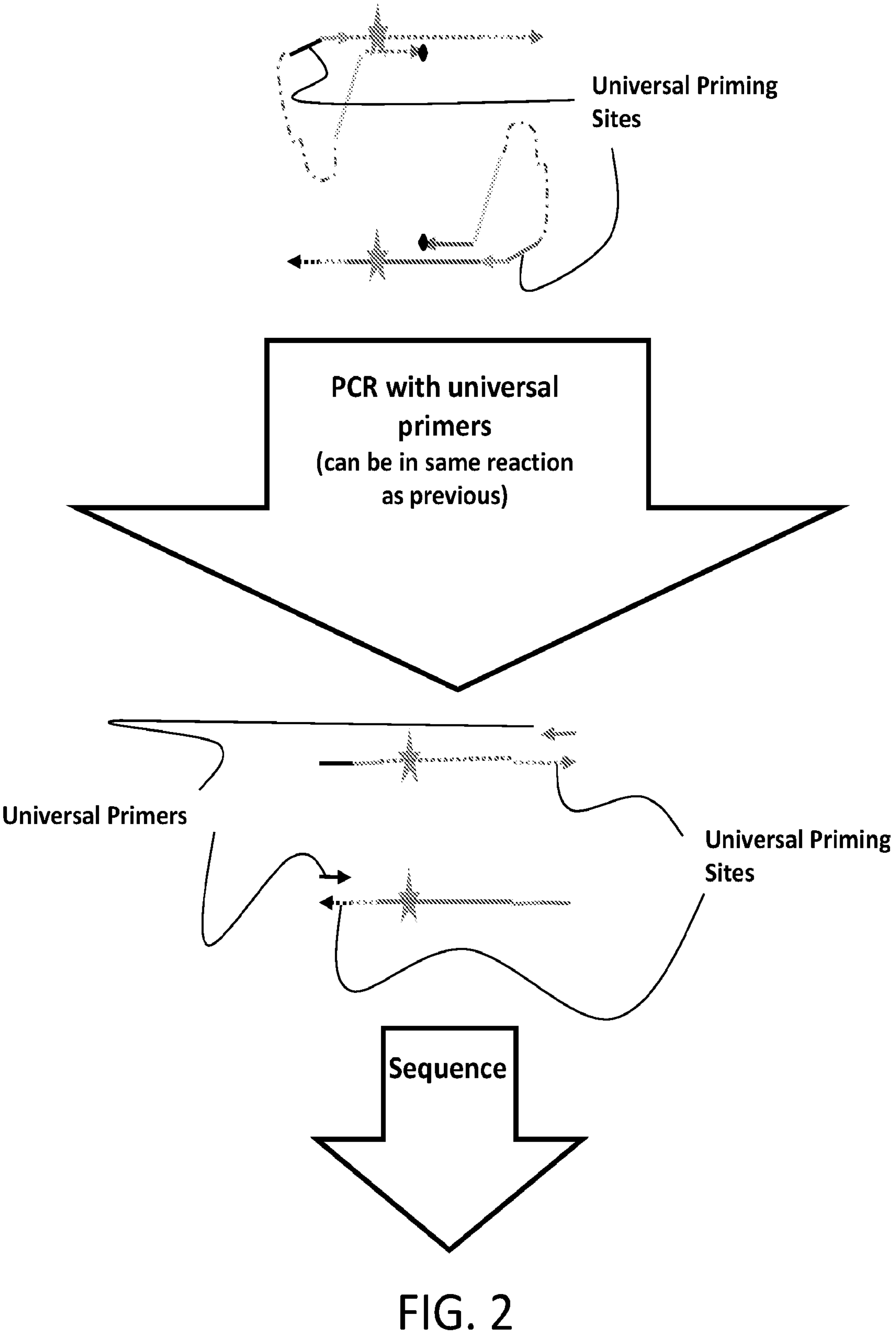
FIG. 2 illustrates amplification methods of linked target captured nucleic acids.

The invention generally relates to methods for targeted capture and analysis of double stranded breaks in DNA, especially for analysis of efficiency and specificity of genome editing systems. Linked target capture techniques are used wherein linked target capture probes including a universal primer and a target-specific probe are used and reactions occur under conditions that require the target-specific probe to bind in order to permit binding of the universal primer. Universal priming sites can be ligated onto the ends of post-editing (e.g., cleavage and sequence insertion) fragments of genomic DNA. The target-specific portion of the linked target capture probe can then be designed to be specific to the target break point of the DNA, the inserted tag sequence, or a combination of the two. By enriching tag sequences alone or along with target sites, information regarding incorporation rate and off-target incorporation can be obtained. That information is essential to assessing existing and future techniques in the burgeoning field of genome editing. Linked-target capture and associated amplification and sequencing techniques using linked molecules are contemplated herein as described in U.S. Pat. Pub. 20190106729, incorporated herein by reference. Tag sequences may be specifically designed for evaluation or may be functional sequences intended for use in genome modification. The target-specific probes targeting the tag sequence can be designed to bind to any sequence (evaluation-specific tag or genomic DNA insert) in order to evaluation general performance of a genome editing technique or to evaluate performance of a specific modification using a specific insert.

Systems and methods described herein can be used in analyzing any such technique including those relying on CRISPR-associated (Cas) endonuclease, zinc-finger nuclease (ZFN), transcription activator-like effector nuclease (TALEN), or RNA-guided engineered nuclease (RGEN). Programmable nucleases and their uses are described in, for example, Zhang F, Wen Y, Guo X (2014). "CRISPR/Cas9 for genome editing: progress, implications and challenges". Human Molecular Genetics. 23 (R1): R40-6. doi:10.1093/hmg/ddu125; Ledford H (March 2016). "CRISPR: gene editing is just the beginning". Nature. 531 (7593): 156-9. doi:10.1038/531156a; Hsu P D, Lander E S, Zhang F (June 2014). "Development and applications of CRISPR-Cas9 for genome engineering". Cell. 157 (6): 1262-78. doi:10.1016/j.cell.2014.05.010; Boch J (February 2011). "TALEs of genome targeting". Nature Biotechnology. 29 (2): 135-6. doi:10.1038/nbt.1767; Wood A J, Lo T W, Zeitler B, Pickle C S, Ralston E J, Lee A H, Amora R, Miller J C, Leung E, Meng X, Zhang L, Rebar E J, Gregory P D, Urnov F D, Meyer B J (July 2011). "Targeted genome editing across species using ZFNs and TALENs". Science. 333 (6040): 307. doi:10.1126/science.1207773; Carroll, D (2011). "Genome engineering with zinc-finger nucleases". Genetics Society of America. 188 (4): 773-782. doi:10.1534/genetics.111.131433; Urnov, F. D., Rebar, E. J., Holmes, M. C., Zhang, H. S., & Gregory, P. D. (2010). "Genome Editing with Engineered Zinc Finger Nucleases". Nature Reviews Genetics. 11 (9): 636-646. doi:10.1038/nrg2842, the contents of each of which are incorporated herein by reference.

Existing techniques for identifying double strand breaks and evaluating genome editing tools are described in U.S. Pat. Nos. 9,822,407 and 9,850,484, incorporated herein by reference and back-end sequencing and analysis techniques described therein may be used with the linked target capture methods described herein for the analysis of double strand breaks and insertion efficiency.

Figure 4:
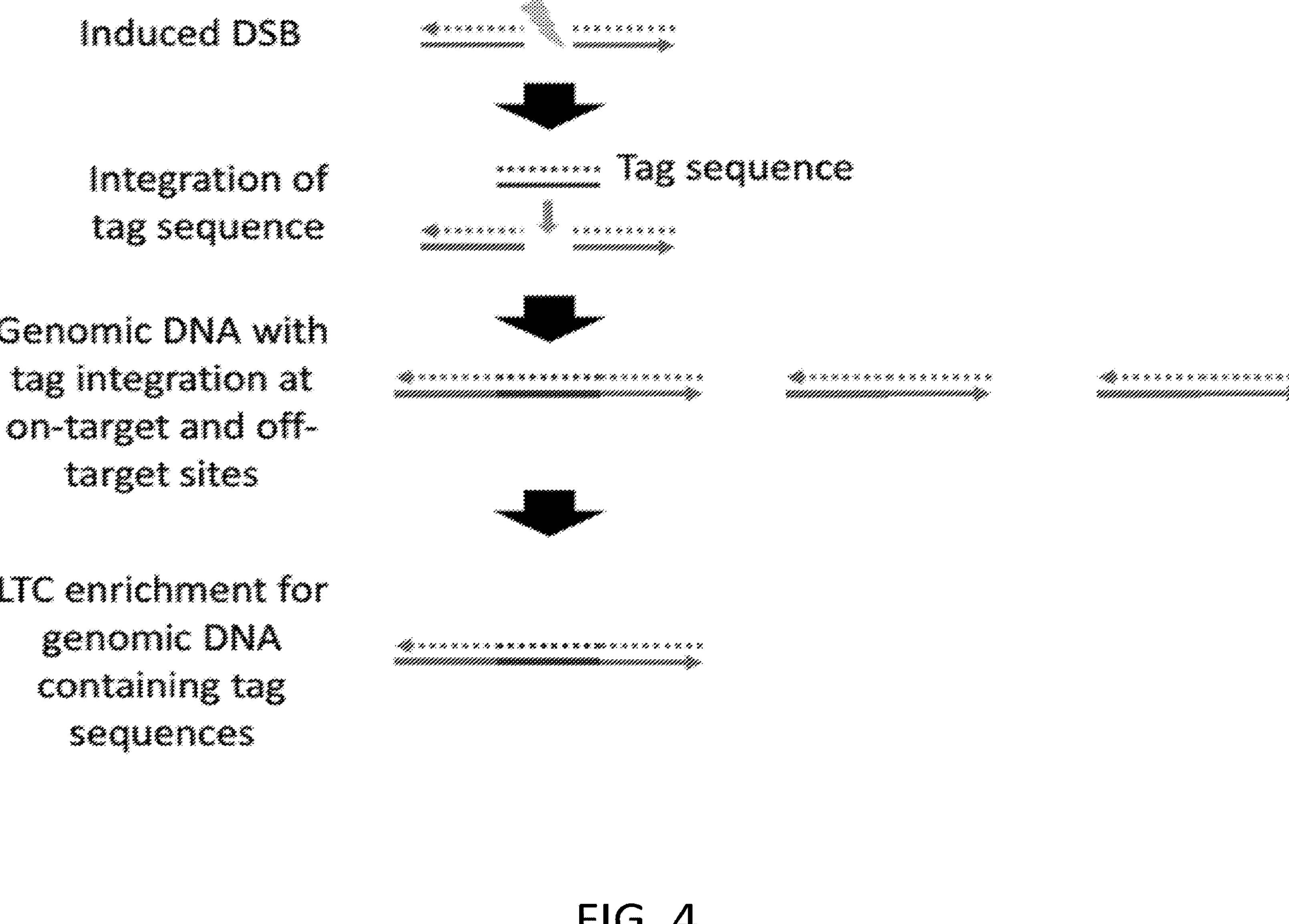
FIG. 4 shows exemplary tag sequence incorporation and induced double stranded cleavage of DNA.

An exemplary double-stranded cleavage and tag insertion is shown in FIG. 4. Any of the discussed methods (e.g., CRISPR-Cas RNA-guided nucleases (RGNs), TALEN (transcription activator-like effector nucleases), and ZFN (zinc finger nucleases)) may be used to introduce a double stranded break. After cleavage, a designed tag sequence may be integrated as shown in FIG. 4. Tag integration can be achieved through methods such as those described in Tsai S. Q., Zheng Z., Nguyen N. T., Liebers M., Topkar V. V., et al. (2015) GUIDE-seq enables genome-wide profiling of off-target cleavage by CRISPR-Cas nucleases. Nat Biotechnol 33: 187-197, incorporated herein by reference. Tag modifications (such as 5' phosphates and 2 phosphorothioate bonds at each end) can be used to increase tag integration rates.

Assuming imperfect cleavage and integration, some target fragments will not have been cleaved or had successful integration of the tag sequence, some will have had successful integration of the tag sequence, and some tag sequences will have been integrated at off target sites. The linked target capture (LTC) techniques described herein can then be used to determine the rates of those outcomes.

Figure 5:
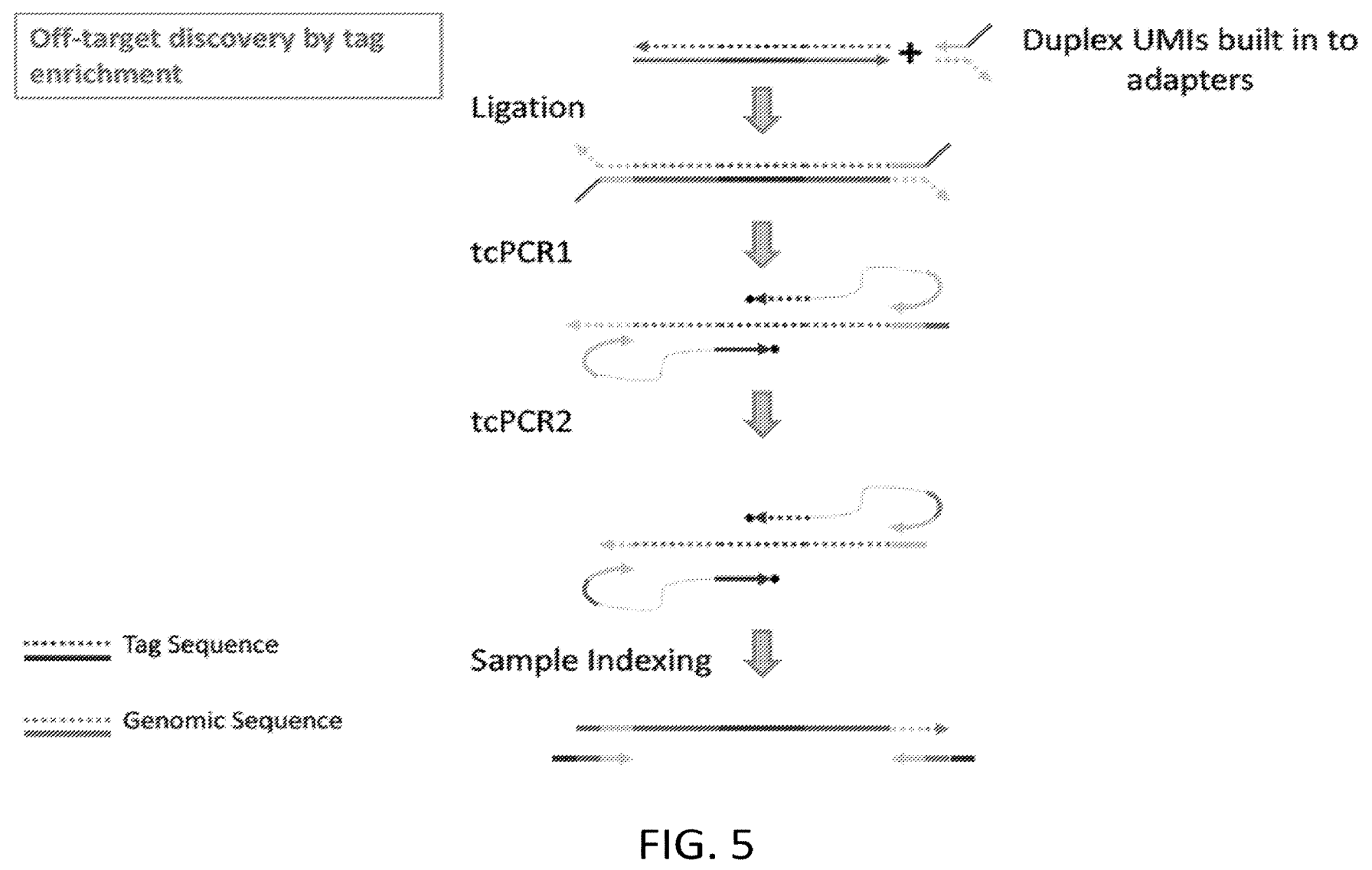

In certain embodiments, as shown in FIG. 5, linked target capture probes are used having a tag-specific probe linked to a universal primer. Before probe binding and amplification, adapters containing universal priming sites are ligated to the sample fragments, thereby providing a target site for the universal primer. The ligated adapters can include unique molecular identifiers (UMI) or other barcode sequences that can be later used to determine the originating molecule from which a sequence was eventually derived. Such information can be used to determine consensus sequences for individual molecules and provide more accurate quantification of cleavage and on-target and off-target incorporation rates. Barcodes can be included on the stem portion of a y-adapter or on the non-complimentary portion of the y-adapter in order to preserve sense-specific tag information. Similarly, the universal priming site can be located on the stem or the y portion of the adapter. In certain embodiments, a stem location is preferred in order to locate the target sites of the linked target capture probe closer together for improved function. In such embodiments, despite the loss of sense-specific tag information, error reducing benefits are still achieved as discussed in U.S. application Ser. No. 16/239,100, incorporated herein by reference.

For off-target discovery by tag enrichment, the target-specific probes preferentially bind the inserted tag sequence. Using linked target capture techniques as discussed below, amplification only occurs where both of the linked probes bind in relatively close proximity to each other along the fragment. The linked probes can include another universal PCR priming sequence (different than the ligated adapter's site) such that, after a few cycles of amplification using linked probes, sample indexing can occur and more robust amplification using conventional universal PCR primers can be used to create a sequencing library. The linked probes, being specific for the tag, should capture and amplify any tag sequence along with the immediately flanking genomic DNA sequence between the tag and the ligated universal priming site. Accordingly, through sequencing and subsequent analysis, the comparative number of tags incorporated at the correct site, incorporated off-target, and not incorporated can be assessed, thereby providing an evaluation of the specificity and efficiency of the cleavage and incorporation techniques being used in the prospective genome editing tool.

Off-target discovery can be combined with flanking sequence enrichment as shown in FIG. 6. Linked target capture and amplification techniques are performed similarly as with those shown in FIG. 5 but different probe-dependent primers (PDPs) are used. Both PDPs include universal primers complimentary to the ligated adapter sequence but the target-specific probes preferentially bind different targets. One target-specific probe binds a tag-specific sequence while the other binds a portion of the genomic DNA flanking the intended incorporation site. The resulting sequence captures should exclude unincorporated tags as well as off-target incorporations, capturing only the correctly incorporated target. In certain embodiments, mismatches with the target-specific probe may be tolerated thereby capturing incorporation errors that may be off-target by a few nucleotides or otherwise cause unintended alterations at the breakpoint.

PDPs can also be used that include target-specific probes that target both sides of the genomic DNA flanking the breakpoint, thereby capturing all genomic fragments including the intended breakpoint. The captured molecules should include genomic DNA in which a tag sequence was successfully incorporated as well as genomic DNA that was not cleaved or was repaired without incorporation. Accordingly, double stranded cleavage and sequence incorporation efficiency can be evaluated for the genome editing tool being tested.

Figure 7:
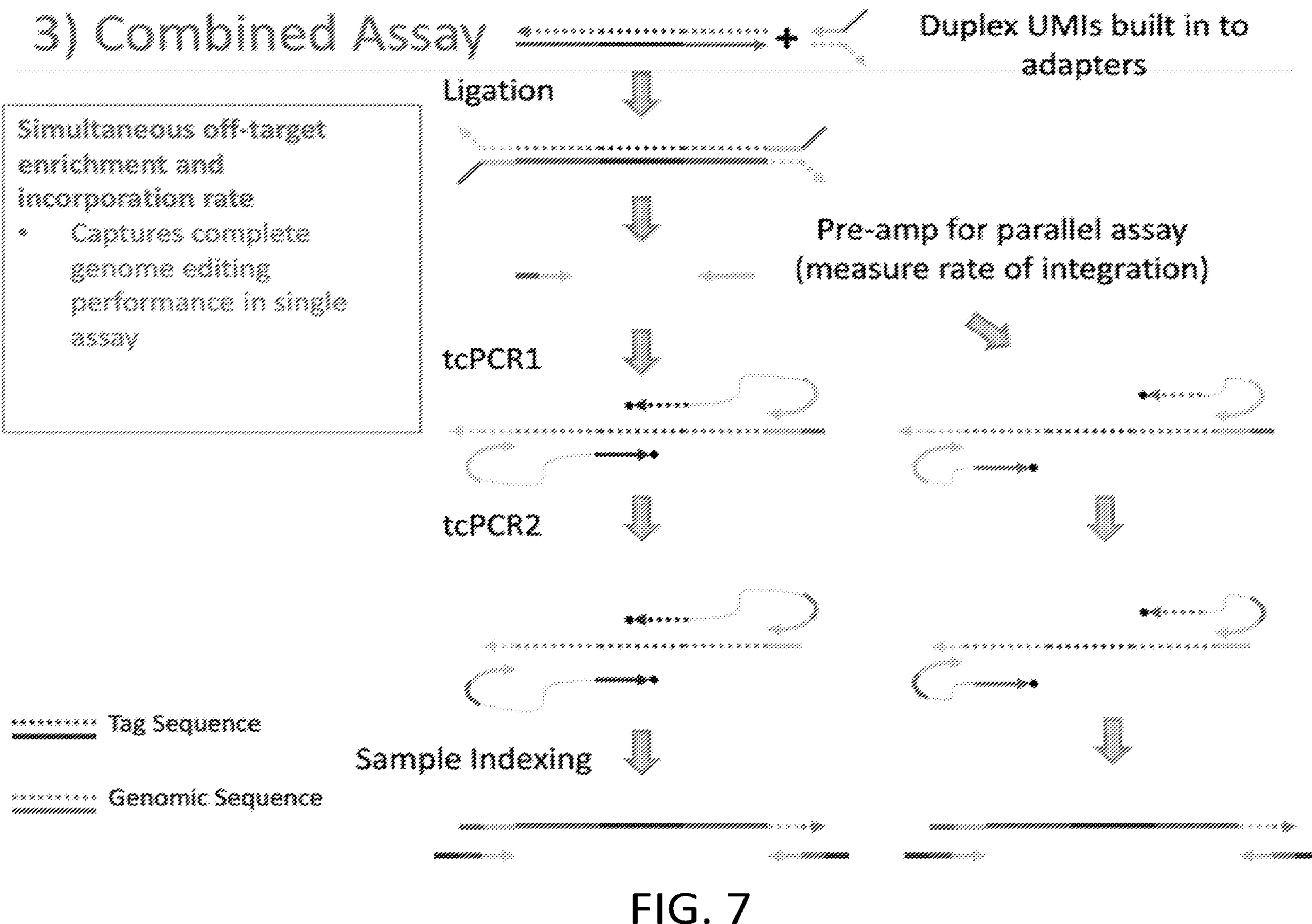
FIG. 7 shows an exemplary combined workflow using HIDN-Seq and linked target capture probe sets specific to the tag sequence and the breakpoint-flanking genomic DNA region.
Figure 8:
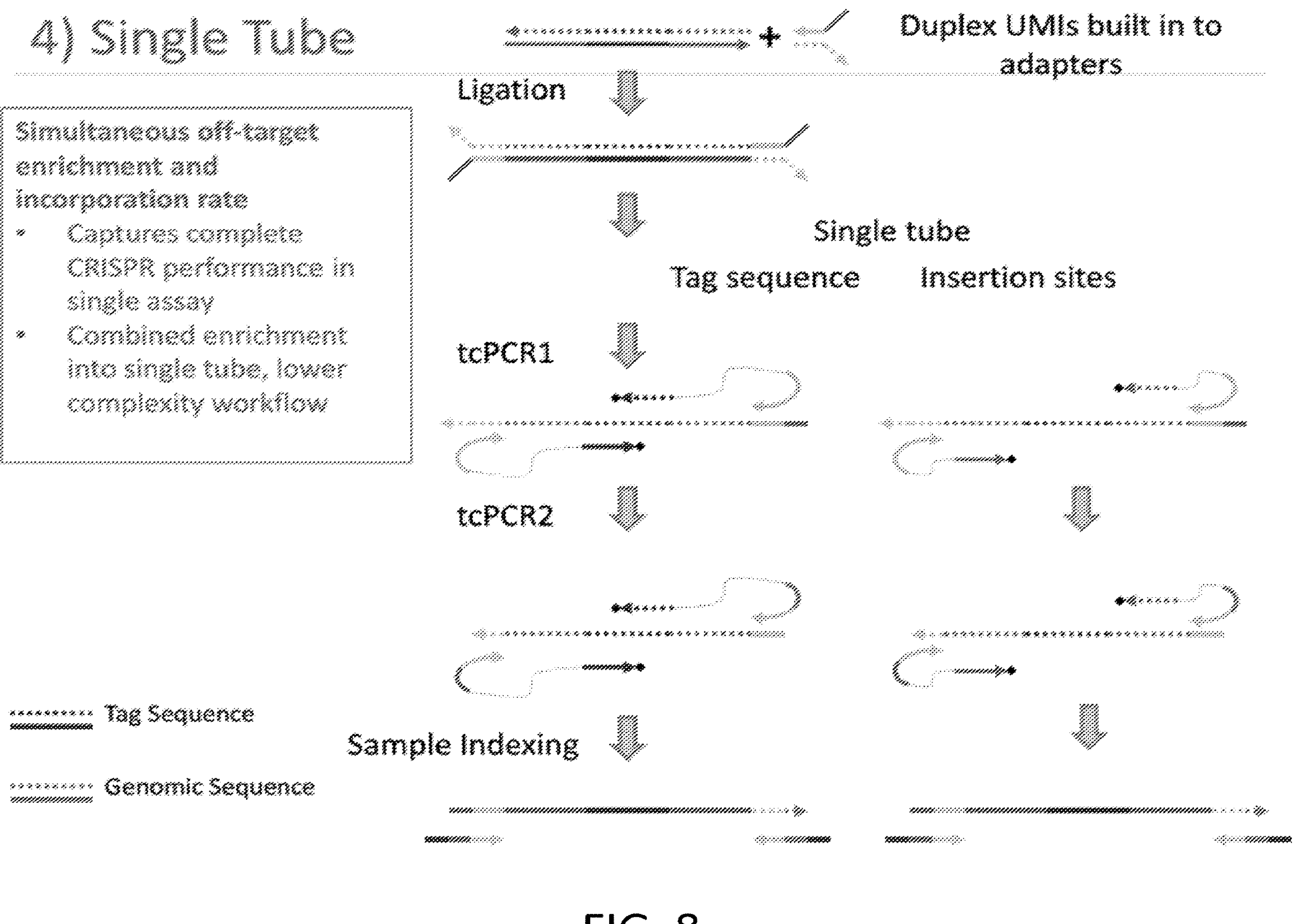
FIG. 8 shows an exemplary combined workflow using HIDN-Seq and linked target capture probe sets specific to the tag sequence and the breakpoint-flanking genomic DNA region performed in a single tube.

The methods can be combined as shown in FIG. 7 where adapters are ligated to the fragments and probes targeting both ends of both the tag insert and the breakpoint-flanking genomic DNA sequence are used. Pre-amplification can be used in such assays to measure the rate of integration. Such assays can simultaneously provide off-target incorporation and on-target incorporation rates giving a complete genome editing performance evaluation in a single assay. As shown in FIG. 8 the combined assay can be performed in a single tube to reduce workflow complexity.

Figure 9:
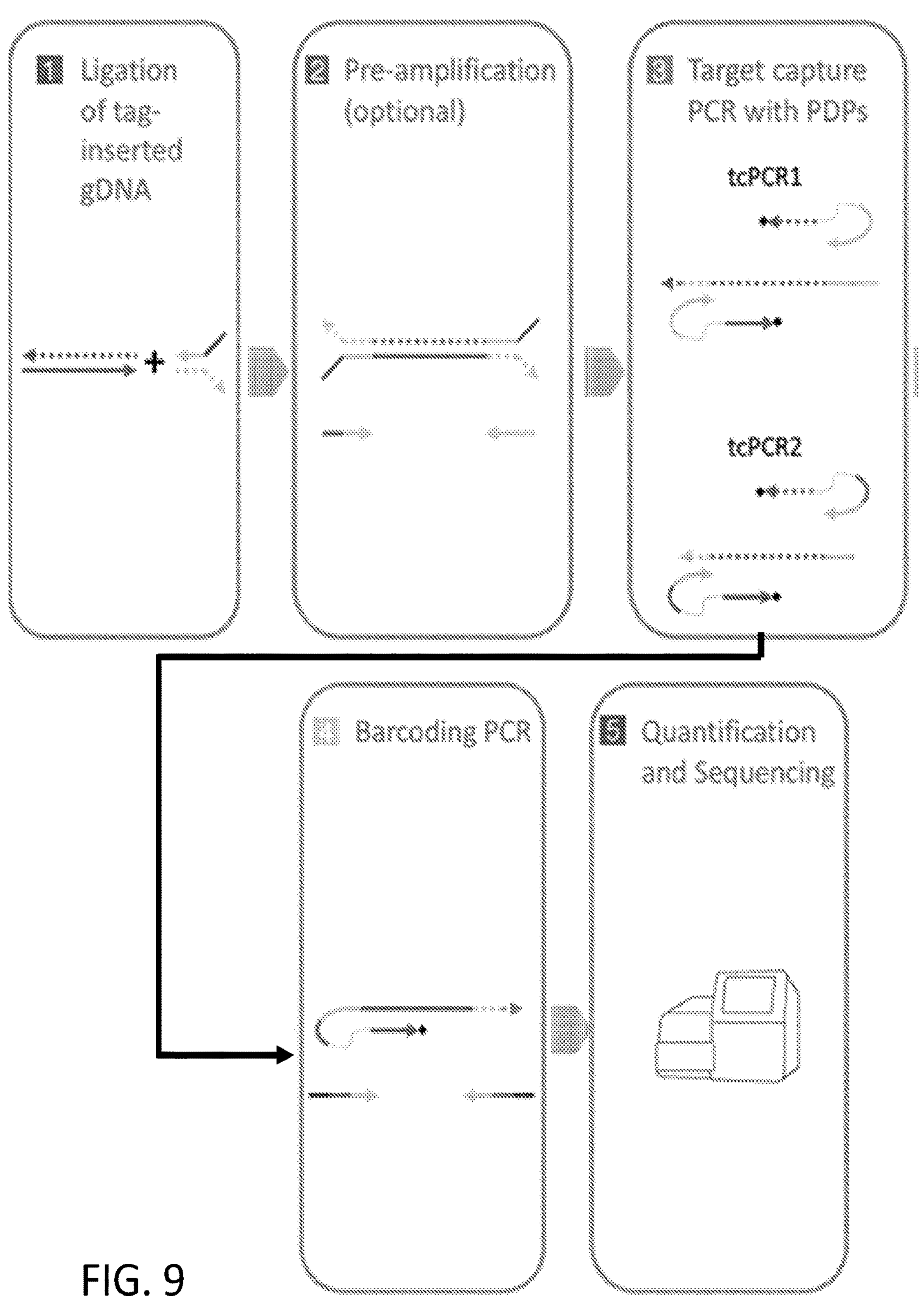
FIG. 9 shows an exemplary workflow using HIDN-Seq with barcoding PCR and quantification and sequencing.

An exemplary method with back-end analysis is shown in FIG. 9. After targeted cleavage and tag sequence incorporation as shown in FIG. 4, adapters are ligated to the ends of the tag-inserted genomic DNA. The adapters include priming sites and optional barcodes. Pre-amplification using primers specific to the adapters is optionally used. Target capture is performed using linked target capture probes as discussed with reference to FIGS. 5-8. A barcoding PCR is used followed by DNA quantification and sequencing. Sequence analysis can be optionally used to then determine consensus sequences for each uniquely-identified molecule. The raw sequencing data or the collapsed reads can then be analyzed to determine, depending on the linked target capture probes used, the relative amount of genomic DNA unmodified at the target breakpoint, unincorporated tag sequence, on-target incorporation, and/or off-target incorporation. Any sequencing technique can be used as well as any known sequence analysis/comparison techniques or software.

Linked target capture methods may include solution-based capture of genomic regions of interest for targeted DNA sequencing. FIGS. 1 and 2 illustrate exemplary methods of solution-based target capture. Universal priming sites and optional barcodes (which may be sense specific) are ligated to extracted DNA. The ligated DNA product is then denatured and bound with linked target capture probes comprising a universal primer linked to a target specific probe. Target capture is performed at a temperature where the universal primers cannot bind alone unless local concentration is high due to the binding of the target probe. Strand displacing polymerase (e.g., Taq, BST, phi29, or SD) is then used to extend the target-bound linked probes. The target probe is blocked from extension as indicated by the black diamond in FIGS. 1 and 2 so that extension only occurs along the bound universal primer, copying the bound target nucleic acid strand that remains linked to the target primer. A number of linked-PCR extension cycles can then be used to amplify the target sequences. PCR can then be performed using universal primers corresponding to the universal priming sites from the linked target capture probes to amplify one or both strands of the target nucleic acid. This PCR step can be performed in the same reaction without the need for a cleanup step. The amplified target sequence can then be sequenced as described above. No gap is required between the linked capture probes when used in opposite directions although a gap is possible. The capture probes may be produced using universal 5'-linkers by joining the universal primers to a pre-made capture probe. The capture probes can be joined by click chemistry or other means as described below In some embodiments, nucleic acids may be fragmented or broken into smaller nucleic acid fragments. Shorter fragments, achieved before ligation of the adapters, can help to shorten the distance the linked probes are required to span, thereby increasing binding and enrichment efficiency. Nucleic acids, including genomic nucleic acids, can be fragmented using any of a variety of methods, such as mechanical fragmenting, chemical fragmenting, and enzymatic fragmenting. Methods of nucleic acid fragmentation are known in the art and include, but are not limited to, DNase digestion, sonication, mechanical shearing, and the like (J. Sambrook et al., "Molecular Cloning: A Laboratory Manual", 1989, 2.sup.nd Ed., Cold Spring Harbour Laboratory Press: New York, N.Y.; P. Tijssen, "Hybridization with Nucleic Acid Probes—Laboratory Techniques in Biochemistry and Molecular Biology (Parts I and II)", 1993, Elsevier; C. P. Ordahl et al., Nucleic Acids Res., 1976, 3: 2985-2999; P. J. Oefner et al., Nucleic Acids Res., 1996, 24: 3879-3889; Y. R. Thorstenson et al., Genome Res., 1998, 8: 848-855). U.S. Patent Publication 2005/0112590 provides a general overview of various methods of fragmenting known in the art.

Probe-dependent primers, used for target capture techniques discussed herein can have a 5' end of a target-specific DNA probe (e.g., complimentary to a portion of the tag insert sequence or a flanking portion of genomic DNA sequence at the breakpoint) linked to the 5' end of a universal primer. The DNA probe may include an inverted dT, C3 spacer or other blocking moiety at its 3' end to prevent extension of the DNA probe in favor of extension of the subsequently bound universal primer brought into close proximity to the target nucleic acid fragment by the DNA probe binding to a complementary target sequence in the fragment. Primers and probes may be synthesized separately and then linked using the techniques discussed below.

While target-specific sequences are preferred for the linked target capture probes, in certain embodiments, the 5' end of the universal primer (with an optional barcode as discussed below) can be attached to the 5' end of a probe molecule that may consist of any protein, nucleic acid, or other molecule showing a binding affinity for a specific-target sequence or target feature in a nucleic acid. The probe molecule may be a DNA or RNA binding probe and can be synthesized or isolated separately from the primer (e.g., universal primer) before being linked together using, for example, click chemistry, biotin/streptavidin binding or derivatives such as dual biotin and traptavidin, PEG, immuno-PCR chemistries such as gold nanoparticles, chemical cross-linking or fusion proteins, or direct linking of proteins/antibodies to the DNA primer sequence. Linking methods are discussed in more detail below.

Exemplary DNA or RNA binding probes can include DNA or RNA probes for targeting a specific DNA or RNA sequence. Zinc finger domains, TAL effectors, or other sequence specific binding proteins may be engineered and linked to universal adapters or primers to create probe-dependent primers or adapters as detailed herein to target specific DNA or RNA sequences. Methyl-CpG-binding domains (MBD) or antibodies (as used in methylated DNA immunoprecipitation) may be linked to adapters or primers to target methylated sequences. For use in the present systems and methods, the target-specific probe need only preferentially bind a desired portion of the integrated tag or the breakpoint flanking genomic DNA sequence. In certain embodiments, the tag may include a feature (e.g., methylated sequence) targetable using a specific probe.

Probe-dependent primers can be made by linking together a universal primer and a target-specific probe with a linking modification. The probe may be synthesized directly with the linking modification. In cases where this is not possible, such as in array synthesized probes, linker modifications can be added by PCR. Probes may be synthesized in arrays on silicon chips and then amplified as opposed to making large quantities in column-based synthesis. Array-based probes containing target sequencing and universal priming sites may be amplified by a universal primer that contains a linking modification. Array-based oligos can be converted into linked target capture probes by adding a 5' linker modification for example by post-synthesis PCR. The 3' blocker can be replaced by a frayed primer end. After amplification, the modified probe can be linked to a universal primer and used as a probe-dependent primer.

In certain embodiments, the linking molecule may be a streptavidin molecule and the fragments to be linked may comprise biotinylated nucleic acid. In embodiments where linked primers are used to create the linked nucleic acid fragments through amplification, the primers may be biotinylated and joined together on a streptavidin molecule. For example, 4 fragments may be joined together on a tetramer streptavidin. More than four molecules could be joined through the formation of concatemers, for example. In certain methods of the invention, two or more nucleic acid fragments may be linked through click chemistry reactions. See Kolb, et al., Click Chemistry: Diverse Chemical Function from a Few Good Reactions, Angew Chem Int Ed Engl. 2001 Jun. 1; 40(11):2004-2021, incorporated herein by reference.

Linking molecules, for example and of several known nanoparticles, may link large numbers of fragments including hundreds or thousands of fragments and/or DNA binding proteins in a single linked molecule. One example of a linking nanoparticle may be polyvalent DNA gold nanoparticles comprising colloidal gold modified with thiol capped synthetic DNA sequences on their surface. See, Mirkin, et al., 1996, A DNA-based method for rationally assembling nanoparticles into macroscopic materials, Nature, 382:607-609, incorporated herein by reference. The surface DNA sequences may be complimentary to the desired template molecule sequences or may comprise universal primers.

The linking molecule may also serve to separate the nucleic acid fragments. In preferred embodiments, the fragments are oriented to prevent binding there between. With the linker creating spatial separation and orientation of the fragments controlled, collapsing or binding between the fragments can be avoided and prevented.

In some embodiments the linkers may be polyethylene glycol (PEG) or a modified PEG. A modified PEG, such as DBCO-PEG4, or PEG-11 may be used to join the two adapters or nucleic acids. In another example, N-hydroxysuccinimide (NHS) modified PEG is used to join the two adapters. See Schlingman, et al., Colloids and Surfaces B: Biointerfaces 83 (2011) 91-95. Any oligonucleotide or other molecule may be used to join adapters or nucleic acids.

In some embodiments, aptamers are used to bind two probes. Aptamers can be designed to bind to various molecular targets, such as primers, proteins, or nucleic acids. Aptamers may be designed or selected by the SELEX (systematic evolution of ligands by exponential enrichment) method. Aptamers are nucleic acid macromolecules that specifically bind to target molecules. Like all nucleic acids, a particular nucleic acid ligand, i.e., an aptamer, may be described by a linear sequence of nucleotides (A, U, T, C and G), typically 15-40 nucleotides long. In some preferred embodiments, the aptamers may include inverted bases or modified bases. In some embodiments, aptamers or modified apatmers, include at least one inverted base or modified base.

It should be appreciated that the linker may be composed of inverted bases, or comprise at least one inverted base. Inverted bases or modified bases may be acquired through any commercial entity. Inverted bases or modified bases are developed and commercially available. Inverted bases or modified bases may be incorporated into other molecules. For example, 2-Aminopurine can be substituted in an oligonucleotide. 2-Aminopurine is a fluorescent base that is useful as a probe for monitoring the structure and dynamics of DNA. 2,6-Diaminopurine (2-Amino-dA) is a modified base can form three hydrogen bonds when base-paired with dT and can increase the Tm of short oligos. 5-Bromodeoxyuridine is a photoreactive halogenated base that can be incorporated into oligonucleotides to crosslink them to DNA, RNA or proteins with exposure to UV light. Other examples of inverted bases or modified bases include deoxyUridine (dU), inverted dT, dideoxycytidine (ddC), 5-methyl deoxyCytidine, or 2'-deoxylnosine (dI). It should be appreciated that any inverted or modified based can be used in linking template nucleic acids.

In preferred embodiments, the linker comprises a molecule for joining two primers or two nucleic acid fragments. The linker may be a single molecule, or a plurality of molecules. The linker may comprise a few inverted bases or modified bases, or entirely inverted bases or modified bases. The linker may comprise a both Watson-Crick bases and inverted or modified bases.

It should be appreciated that any spacer molecule or linking molecule may be used in the present invention. In some embodiments, the linker or spacer molecule may be a lipid or an oligosaccharide, or an oligosaccharide and a lipid. See U.S. Pat. No. 5,122,450. In this example, the molecule is preferably a lipid molecule and, more preferably, a glyceride or phosphatide which possesses at least two hydrophobic polyalkylene chains.

The linker may be composed of any number of adapters, primers, and copies of fragments. A linker may include two identical arms, where each arm is composed of binding molecules, amplification primers, sequencing primers, adapters, and fragments. A linker may link together any number of arms, such as three or four arms. It should be appreciated that in some aspects of the invention, nucleic acid templates are linked by a spacer molecule. The linker in the present invention may be any molecule or method to join two fragments or primers. In some embodiments, polyethylene glycol or a modified PEG such as DBCO-PEG4 or PEG-11 is used. In some embodiments the linker is a lipid or a hydrocarbon. In some embodiments a protein may join the adapters or the nucleic acids. In some embodiments, an oligosaccharide links the primers or nucleic acids. In some embodiments, aptamers link the primers or nucleic acids.

When the fragments are linked, the copies are oriented to be in phase so to prevent binding there between.

In certain embodiments, a linker may be an antibody. The antibody may be a monomer, a dimer or a pentamer. It should be appreciated that any antibody for joining two primers or nucleic acids may be used. For example, it is known in the art that nucleoside can be made immunogenic by coupling to proteins. See Void, B S (1979), Nucl Acids Res 7, 193-204. In addition, antibodies may be prepared to bind to modified nucleic acids. See Biochemical Education, Vol. 12, Issue 3.

The linker may stay attached to the complex during amplification. In some embodiments, the linker is removed prior to amplification. In some embodiments, a linker is attached to a binding molecule, and the binding molecule is then attached to an amplification primer. When the linker is removed, the binding molecule or binding primer is exposed. The exposed binding molecule also attaches to a solid support and an arch is formed. The linker may be removed by any known method in the art, including washing with a solvent, applying heat, altering pH, washing with a detergent or surfactant, etc.

Methods of the invention include droplet based target capture, optionally using universal linked primers, to capture duplex molecules. The droplet based methods depicted in described in U.S. Pat. Pub. 20190106729 but use linked target capture probes as described therein and depicted in FIGS. 1 and 2. Universal primers and optional barcodes (which may be sense specific) are ligated to extracted DNA (e.g., cell-free DNA). An emulsion is created as described above using a duplex template molecule and target capture probes comprising a universal primer linked to a target specific probe. As above, target capture is performed at a temperature where the universal primers cannot bind alone unless local concentration is high due to the binding of the target probe and the capture probes are blocked from extending themselves but include a universal priming site such that universal primers and linked universal primers included in the emulsion can be used to amplify the target nucleic acid to produce a linked duplex molecule comprising both sense and antisense strands of the target nucleic acid. Universal linkers may be omitted to perform target capture alone. The emulsion can then be broken and un-linked template can be digested enzymatically leaving only linked duplex molecules can then seed clusters or otherwise be sequenced as described above.

Figure 3A:
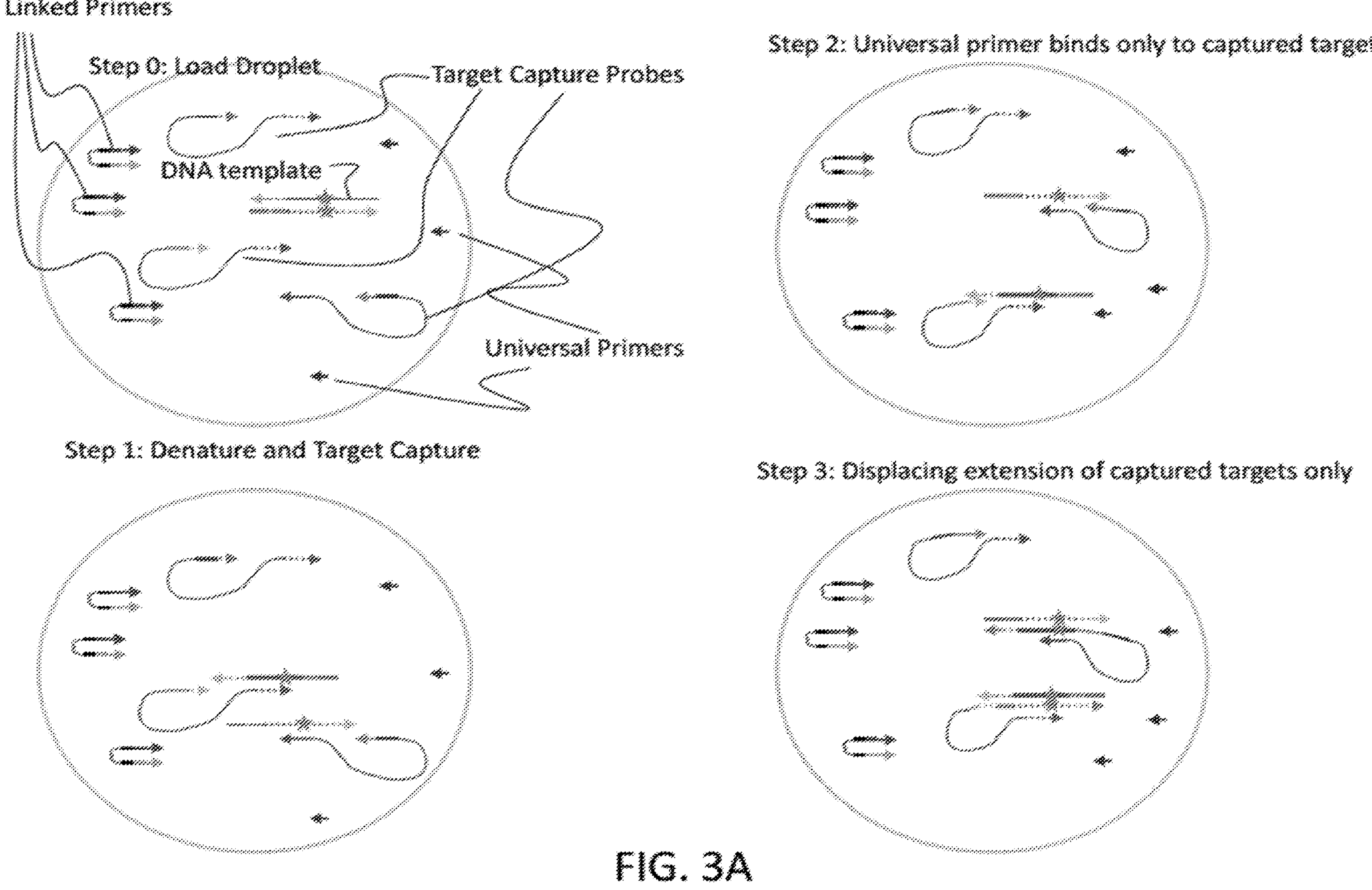
FIGS. 3A and 3B show steps of a droplet-based target capture method of the invention.
Figure 3B:
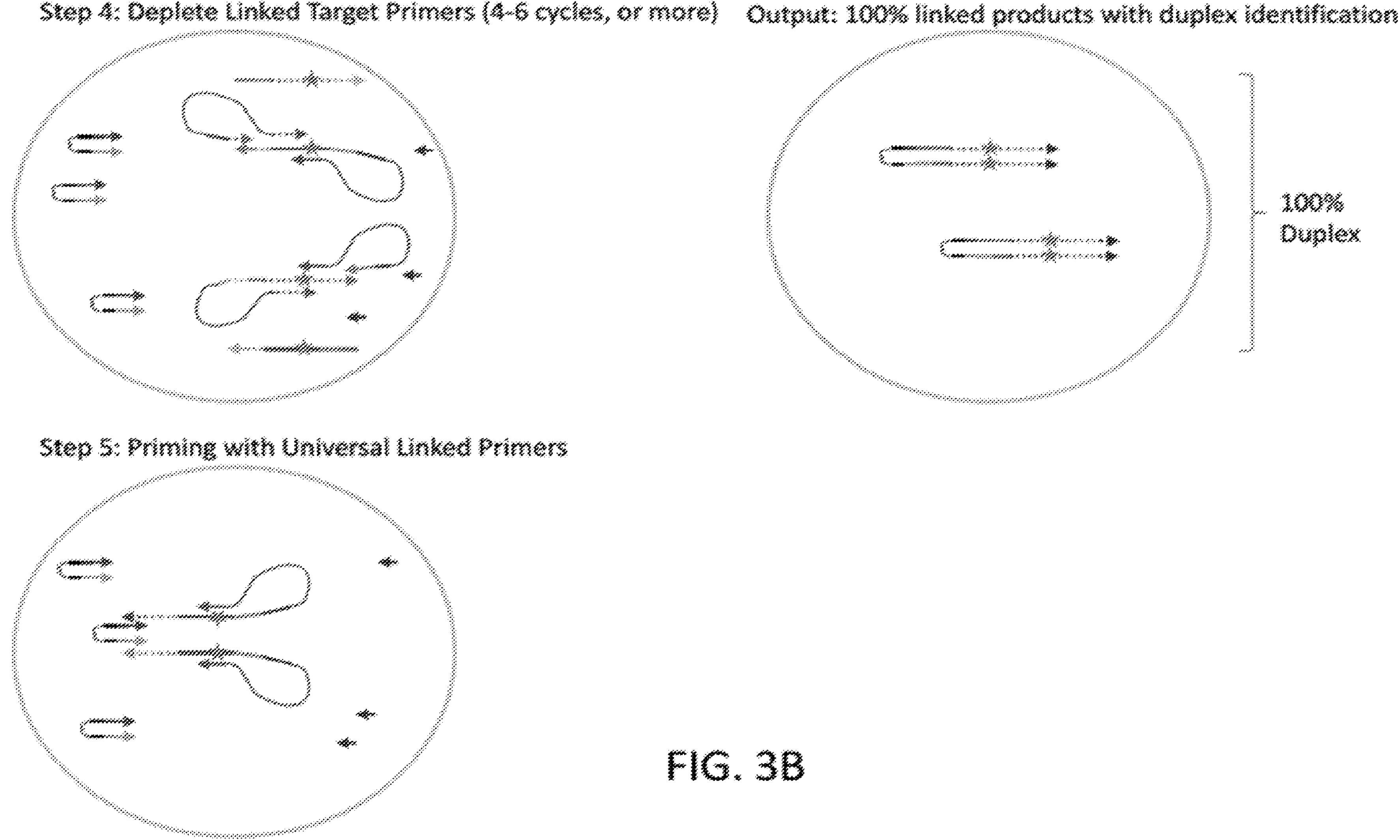

FIGS. 3A and 3B provide additional details of droplet-based target capture methods of the invention. Step 0 in FIG. 3A shows a duplex template molecule with universal priming sites and optional barcodes ligated to it is loaded into a droplet with linked and universal primers and target capture probes. The template DNA is denatured in the droplet and the target capture probes then bind the denatured template strands at a temperature where the universal primer will not bind alone unless the target probe is also bound. The universal primer then only binds to captured targets. Extension with strand displacing polymerase then occurs only on the captured targets. Moving to FIG. 3B, extension cycles are then run (e.g., 4-6 cycles) until the liked target capture probes and primers are exhausted. The resulting extension products are then amplified using the universal linked primers to produce linked duplex molecules with strand specific barcodes. As with the solution-based methods, no gap is required between the linked capture probes when in opposite directions. The linked capture probes can be used in one or both directions if omitting the universal linkers to perform target capture alone. Conventional polymerases can be mixed with strand displacing polymerases within the droplet to carry out the various extension and amplification steps of the method.

EXAMPLES

Example 1: HIDN-Seq on Cas9 Cell Line

Figure 10:
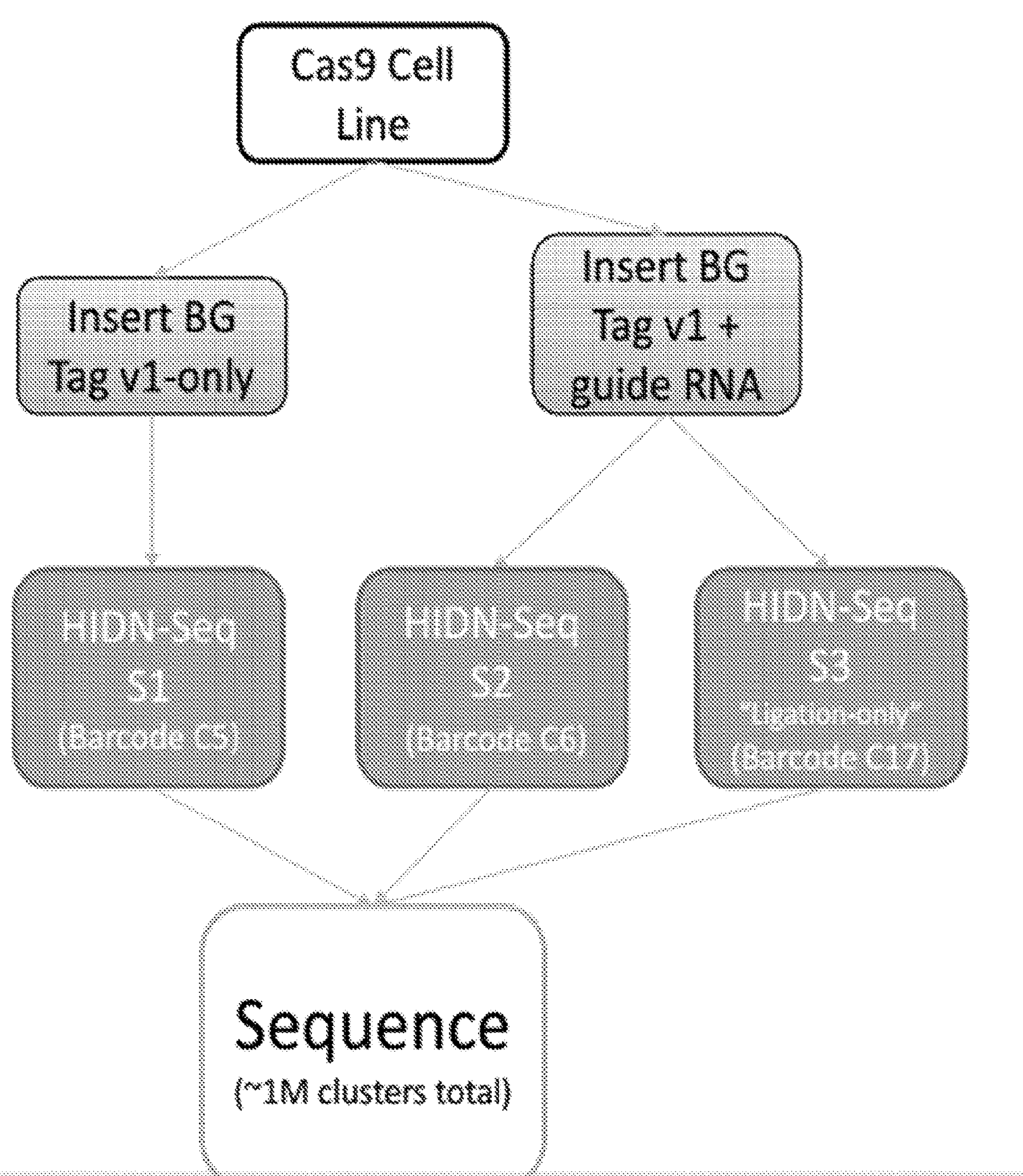
FIG. 10 shows an experimental overview of Example 1.

Using a Cas9 cell line, an insert was added to one group of cells as a control and an insert along with a guide RNA targeting the desired insertion breakpoint was added. HIDN-Seq as detailed above was then performed on the DNA from both cell groups. For the experimental (gRNA+insert) group, linked target capture was performed as described above as well as without PCR amplification after adapter ligation (i.e., directly from ligation into linked target capture amplification, as shown in FIG. 9). The experimental overview is shown in FIG. 10 where S1 represents HIDN-Seq performed on the control DNA (no gRNA added), S2 represents HIDN-Seq with linked target capture as described above S3 represents HIDN-Seq with linked target capture as described but without PCR amplification after adapter ligation. About 1 million clusters were sequenced for all three samples. Results are shown in FIGS. 11 and 12.

Figure 11:
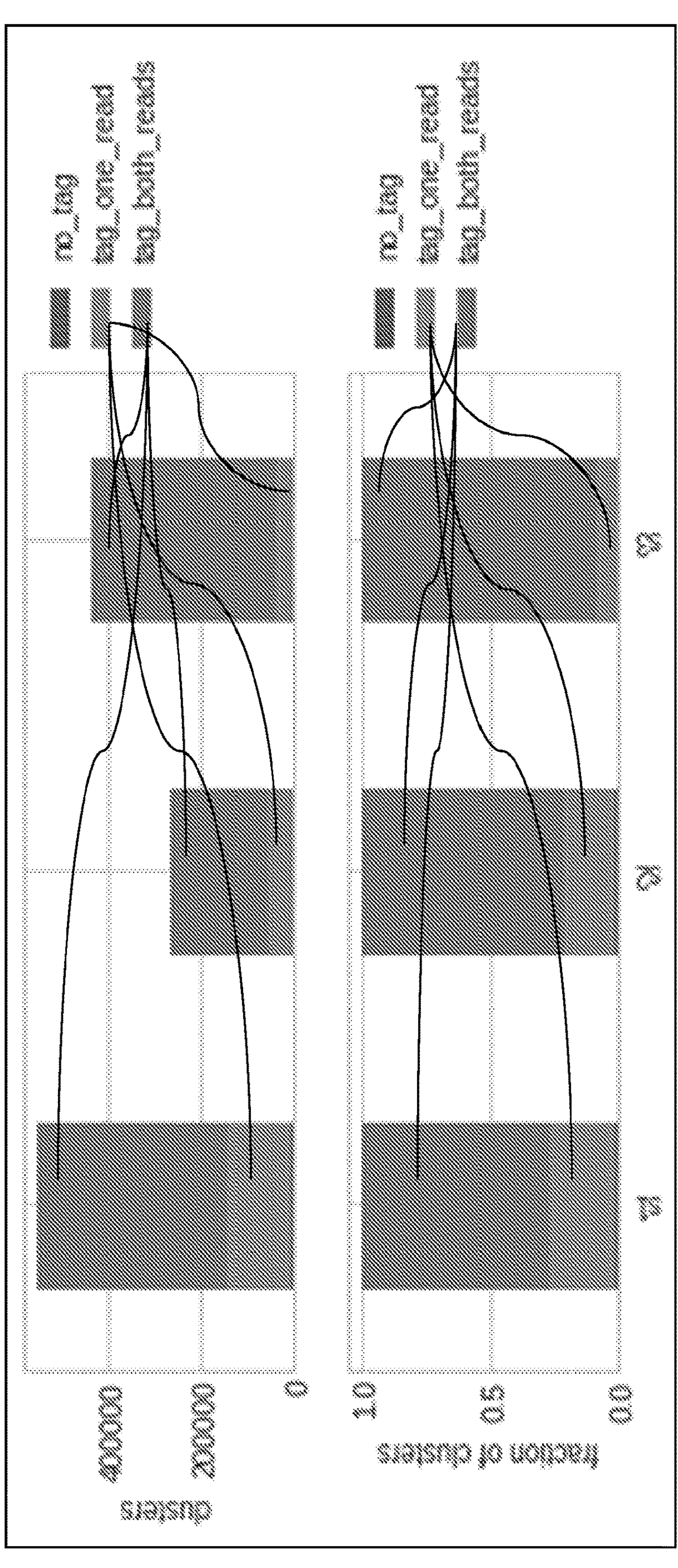
FIG. 11 shows the number and fraction of 51, S2, and S3 clusters containing an intended tag sequence in zero, one, or both reads for Example 1.

FIG. 11 shows the number and fraction of 51, S2, and S3 clusters containing the tag sequence in zero, one, or both reads. As shown, greater than 99% of clusters in each sample contain at least one read with the expected tag sequence (to within an edit distance of 4) meaning that there were essentially no wasted reads.

Figure 12:
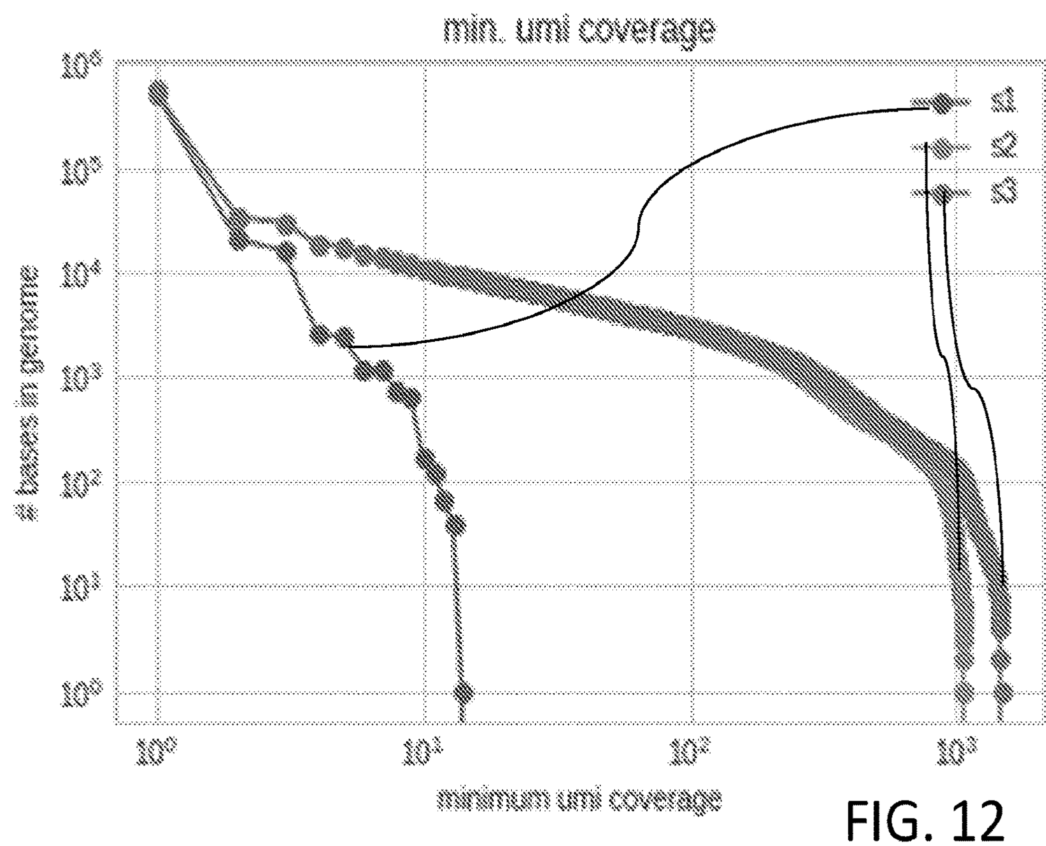
FIG. 12 shows UMI coverage across the genome plotting the number of bases in the genome and minimum UMI coverage for the 51, S2, and S3 groups for Example 1.

FIG. 12 shows UMI coverage across the genome plotting the number of bases in the genome and minimum UMI coverage for the 51, S2, and S3 groups. The 51 (tag only) group had much lower coverage with a maximum coverage of <20, suggesting that only a few cut sites occurred with low integration rate, as expected without a gRNA. The S2 and S3 groups however had much higher coverage in certain regions, suggesting significant integration at multiple sites.

The sequencing results for off-target sites are shown below in Table 1 for S2 and S3 groups. The S1 (tag-only) group had no matches to the gRNA while the S2 and S3 groups had the gRNA sequence found in each of the top 50 coverage regions. The top 20 of each are shown in Table 1. The target sequences are underlined.

TABLE 1

| umi coverage | Reference sequence | Edit dist. to gRNA | chr | start | stop |
|---|---|---|---|---|---|
| | S2 | | | | |
| gRNA: | **GTTGGAGCATCTGAGTCCAG** (SEQ ID NO: 1) | | | | |
| 1029.7 | GATGGAGCAACCGAGTCCAG (SEQ ID NO: 2) | 3 | chr1 | 27592693 | 27592713 |

TABLE 1 -continued

| umi coverage | Reference sequence | Edit dist. to gRNA | chr | start | stop |
|---|---|---|---|---|---|
| 972.8 | GTTGGAGCATCTGAGTCCAG (SEQ ID NO: 1) | 0 | chrX | 67545904 | 67545924 |
| 930.5 | AATGGGGCATCTGAGTCCATG (SEQ ID NO: 3) | 4 | chr17 | 14626783 | 14626804 |
| 598.7 | GTTGGAGAAACTGAGTCCAG (SEQ ID NO: 4) | 2 | chr20 | 46362541 | 46362561 |
| 438.3 | G-GGGAGTATCTGAGTCCAG (SEQ ID NO: 5) | 3 | chr10 | 70535116 | 70535135 |
| 412.1 | GTTGGAGCCTCTGAGTCCAG (SEQ ID NO: 6) | 1 | chr8 | 70014903 | 70014923 |
| 353 | GGAGGAACATCTGAGTCCAG (SEQ ID NO: 7) | 3 | chr6 | 111617768 | 111617788 |
| 379.5 | GGAGGAGCACCTGAGTCCAG (SEQ ID NO: 8) | 3 | chr12 | 122113358 | 122113378 |
| 336.3 | GATGGTGCATCTGACTCCAG (SEQ ID NO: 9) | 3 | chr19 | 39394098 | 39394118 |
| 319.3 | ATTGGAGCCTCTGAGTCCAG (SEQ ID NO: 10) | 2 | chr7 | 22126335 | 22126355 |
| 296.6 | GTGTGGAGTATCCGAGTCCAG (SEQ ID NO: 11) | 3 | chr18 | 26782002 | 26782023 |
| 279 | GATAGGAACATCTGAGACCAG (SEQ ID NO: 12) | 4 | chr1 | 195970287 | 195970308 |
| 283.4 | GATGGAGCTTCTGAGTCCTG (SEQ ID NO: 13) | 3 | chr15 | 32101673 | 32101693 |
| 277.2 | GAAGGATCATCTGAGTCCAG (SEQ ID NO: 14) | 3 | chr7 | 155641561 | 155641581 |
| 221.3 | GGTGAAGAGCATCTGGAGTCCAG (SEQ ID NO: 15) | 4 | chr6 | 110986338 | 110986361 |
| 249.8 | GTAGGAGTATCTGAGTCCAG (SEQ ID NO: 16) | 2 | chr4 | 33488669 | 33488689 |
| 184.8 | GCTGGAGAAACTGAGTCCAG (SEQ ID NO: 17) | 3 | chr10 | 116741326 | 116741346 |
| 163.3 | CCTGGAGC-TCAGAGTCCAG (SEQ ID NO: 18) | 4 | chr17 | 41631352 | 41631371 |
| 139.8 | GTTGGATCATCTGAGTTCAG (SEQ ID NO: 19) | 2 | chr2 | 99538778 | 99538798 |
| 127.6 | GTTGAACCATCTGAGTCCAG (SEQ ID NO: 20) | 2 | chr10 | 69736220 | 69736240 |
| | S3 | | | | |
| gRNA: | **GTTGGAGCATCTGAGTCCAG** (SEQ ID NO: 1) | | | | |
| 1415.4 | GATGGAGCAACCGAGTCCAG (SEQ ID NO: 2) | 3 | chr1 | 27592693 | 27592713 |
| 1126.7 | GTTGGAGCATCTGAGTCCAG (SEQ ID NO: 1) | 0 | chrX | 67545904 | 67545924 |
| 1105.3 | AATGGGGCATCTGAGTCCATG (SEQ ID NO: 3) | 4 | chr17 | 14626783 | 14626804 |
| 638.3 | GTTGGAGAAACTGAGTCCAG (SEQ ID NO: 4) | 2 | chr20 | 46362541 | 46362561 |
| 570.7 | GGAGGAGCACCTGAGTCCAG (SEQ ID NO: 8) | 3 | chr12 | 122113358 | 122113378 |
| 471.7 | GTTGGAGCCTCTGAGTCCAG (SEQ ID NO: 6) | 1 | chr8 | 70014903 | 70014923 |
| 491.2 | G-GGGAGTATCTGAGTCCAG (SEQ ID NO: 5) | 3 | chr10 | 70535116 | 70535135 |
| 451 | ATTGGAGCCTCTGAGTCCAG (SEQ ID NO: 10) | 2 | chr7 | 22126335 | 22126355 |
| 408.1 | GAAGGATCATCTGAGTCCAG (SEQ ID NO: 14) | 3 | chr7 | 155641561 | 155641581 |
| 378.3 | GATGGAGCTTCTGAGTCCTG (SEQ ID NO: 13) | 3 | chr15 | 32101673 | 32101693 |
| 385.8 | GATGGTGCATCTGACTCCAG (SEQ ID NO: 9) | 3 | chr19 | 39394098 | 39394118 |
| 352.9 | GGAGGAACATCTGAGTCCAG (SEQ ID NO: 7) | 3 | chr6 | 111617768 | 111617788 |
| 294.4 | GATAGGAACATCTGAGACCAG (SEQ ID NO: 12) | 4 | chr1 | 195970287 | 195970308 |
| 289.6 | GGTGAAGAGCATCTGGAGTCCAG (SEQ ID NO: 15) | 4 | chr6 | 110986338 | 110986361 |
| 281.1 | GTGTGGAGTATCCGAGTCCAG (SEQ ID NO: 11) | 3 | chr18 | 26782002 | 26782023 |
| 277.8 | GTAGGAGTATCTGAGTCCAG (SEQ ID NO: 16) | 2 | chr4 | 33488669 | 33488689 |

TABLE 1 -continued

| umi coverage | Reference sequence | Edit dist. to gRNA | chr | start | stop |
|---|---|---|---|---|---|
| 230.7 | GTTGGATCATCTGAGTTCAG (SEQ ID NO: 19) | 2 | chr2 | 99538778 | 99538798 |
| 238.6 | GCTGGAGAAACTGAGTCCAG (SEQ ID NO: 17) | 3 | chr10 | 116741326 | 116741346 |
| 203.2 | CCTGGAGC-TCAGAGTCCAG (SEQ ID NO: 18) | 4 | chr17 | 41631352 | 41631371 |
| 167.7 | GAAGGATCACCTGAGTCCAG (SEQ ID NO: 21) | 4 | chr17 | 16212979 | 16212999 |

The double stranded tag sequence used in the experiment were as follows:

```
BG Tag v1 sequence (SEQ ID NO: 22):
/5Phos/C*A*GTGTTTAATTGAGTTGTCATATGTTAATAACGGTATC

A*G*C

BG Tag v1 sequence
(reverse compliment, SEQ ID NO: 23):
/5Phos/G*C*TGATACCGTTATTAACATATGACAACTCAATTAAACA

C*T*G

The forward probe (Tm = 69.1° C.) sequence was
(SEQ ID NO: 24):
CA+GT+GTTTA+ATTGAGTTGTCATATGTTAATAACGG

The reverse probe (Tm = 69.3° C.) sequence was
(SEQ ID NO: 25)
G+CT+GATACCGTTATTAACATATGACAACTCA
```

The tag sequence was chosen such that it had a melting temperature high enough to allow binding of a forward and reverse linked target capture probe. Probe sequences were chosen with high specificity for the tag sequence, but low overlap temperature (for example, less than 60° C.). Locked nucleic acids (LNA's, indicated by '+' prior to the LNA base) were used to achieve a desired probe melting temperature.

Example 2: Tag Enrichment

Figure 13:
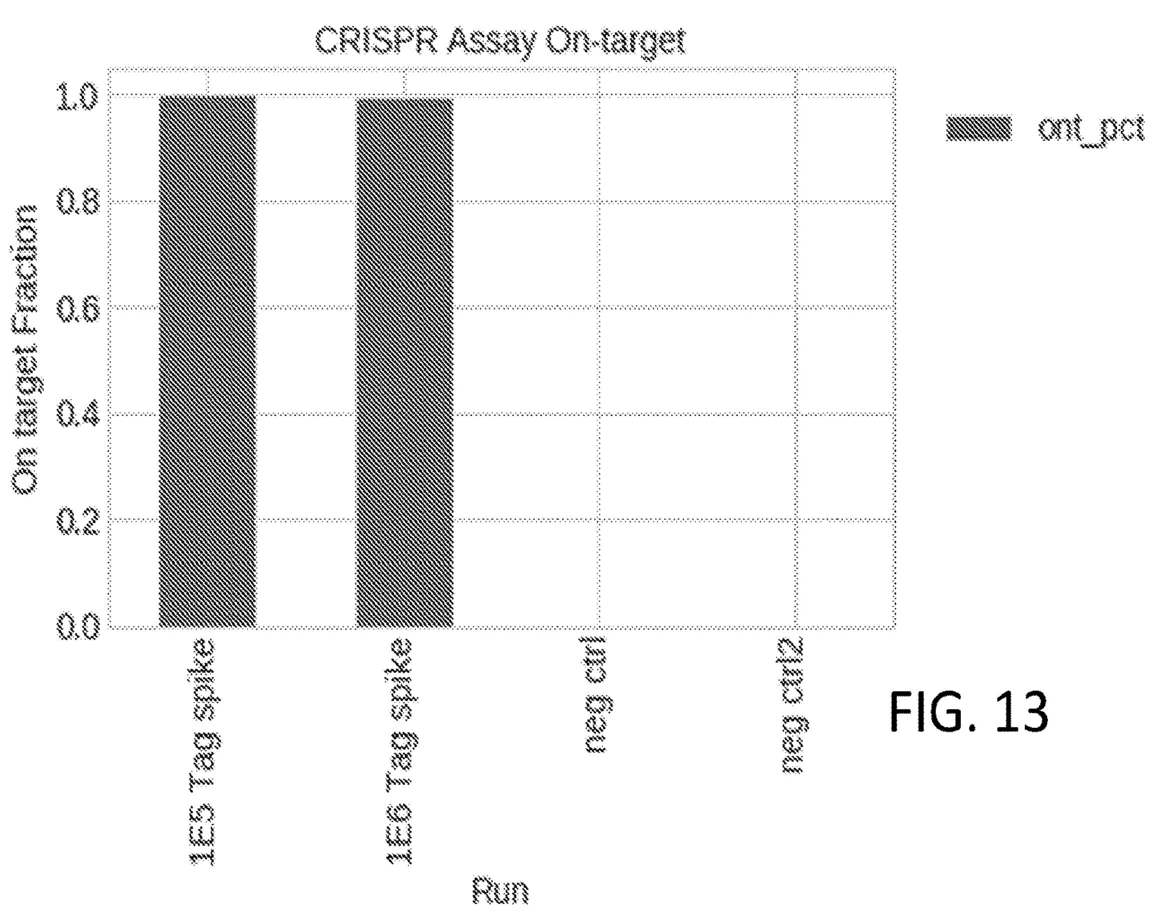
FIG. 13 shows on-target fraction in Example 2 as determined with HIDN-Seq on spiked samples.

Genomic DNA containing tag sequences was spiked into genomic DNA at various amounts and the samples were subjected to HIDN-Seq using forward and reverse probes with tag-specific probes (as shown in FIG. 5). The fraction of sequencing reads containing the tag sequence is >99.8% for both 1E5 and 1E6 tag spike levels as shown in FIG. 13. The genomic flanking sequence of the tag was recovered since linked target capture amplifies the entire insert from the ligation adapter.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A method for detecting double stranded DNA insertion, the method comprising:

ligating universal priming sites onto a plurality of duplex nucleic acid fragments wherein one or more of the plurality of duplex nucleic acid fragments comprise a tag sequence inserted at an insertion site;

denaturing the plurality of ligated duplex nucleic acid fragments to create single stranded nucleic acid fragments comprising universal priming sites;

exposing the single stranded nucleic acid fragments to a first plurality of linked capture probes each comprising a first target probe linked to a first universal primer, wherein the first target probe is complementary to the tag sequence and is blocked from extension, and a second plurality of linked capture probes each comprising a second target probe linked to a second universal primer, wherein the second target probe is complementary to a proximate sequence within 150 nucleotides of the insertion site and is blocked from extension, wherein the exposing step occurs under conditions that require binding of the first or the second target probe to its complementary target to permit binding of the respective linked universal primer to the universal priming site;

extending the first and second universal primers to produce copies of the insertion site and the tag sequence region; and sequencing the copies to determine presence of the tag sequence in the insertion site.

2. The method of claim 1, wherein the proximate sequence does not span the insertion site.

3. The method of claim 1, wherein the extending step uses a strand displacing polymerase.

4. The method of claim 1, further comprising inserting the tag sequence into the insertion site using a genome editing tool.

5. The method of claim 4, wherein the genome editing tool is selected from the group consisting of clustered regularly interspaced short palindromic repeats (CRISPR) and associated enzymes, meganucleases, transcription activator effector-like nucleases, and zinc-finger nucleases.

6. The method of claim 4, further comprising comparing an amount of sequences containing the tag sequence at the insertion site to an amount of sequences containing the insertion site without a tag sequence inserted to determine integration rate of the genome editing tool.

7. The method of claim 4, further comprising comparing an amount of sequences containing the tag sequence at the insertion site to an amount of sequences containing the tag sequence inserted off-target of the insertion site to determine an off-target integration rate for the genome editing tool.

8. The method of claim 1, wherein the melting temperature between the tag sequence and the probe sequence is sufficient to allow binding of the linked capture probes.

9. The method of claim 1, wherein the ligating step further comprises ligating unique barcodes onto the plurality of duplex nucleic acid fragments.

10. The method of claim 9, wherein the unique barcodes are sense specific.

11. The method of claim 1, wherein the first target probe has been linked to the first universal primer using click chemistry.

12. The method of claim 1, further comprising repeating the exposing and extending steps to amplify the genomic region of interest prior to the sequencing step.

13. The method of claim 1, further comprising amplifying the copies using un-linked universal primers prior to the sequencing step.

14. The method of claim 13, wherein the amplifying step comprises PCR.

15. The method of claim 1 wherein the duplex nucleic acid fragments are sheared prior to ligation.

* * * * *

SEQUENCE LISTING

```
<160> NUMBER OF SEQ ID NOS: 25

<210> SEQ ID NO 1
<211> LENGTH: 20
<212> TYPE: DNA
<213> ORGANISM: Unknown
<220> FEATURE:
<223> OTHER INFORMATION: Synthesized

<400> SEQUENCE: 1

gttggagcat ctgagtccag                                                   20


<210> SEQ ID NO 2
<211> LENGTH: 20
<212> TYPE: DNA
<213> ORGANISM: Unknown
<220> FEATURE:
<223> OTHER INFORMATION: Synthesized

<400> SEQUENCE: 2

gatggagcaa ccgagtccag                                                   20
```

<210> SEQ ID NO 3
<211> LENGTH: 21
<212> TYPE: DNA
<213> ORGANISM: Unknown
<220> FEATURE:
<223> OTHER INFORMATION: Synthesized

<400> SEQUENCE: 3
aatggggcat ctgagtccat g 21

<210> SEQ ID NO 4
<211> LENGTH: 20
<212> TYPE: DNA
<213> ORGANISM: Unknown
<220> FEATURE:
<223> OTHER INFORMATION: Synthesized

<400> SEQUENCE: 4
gttggagaaa ctgagtccag 20

<210> SEQ ID NO 5
<211> LENGTH: 20
<212> TYPE: DNA
<213> ORGANISM: Unknown
<220> FEATURE:
<223> OTHER INFORMATION: Synthesized
<220> FEATURE:
<221> NAME/KEY: misc_feature
<222> LOCATION: (2)..(2)
<223> OTHER INFORMATION: n is a, c, g, or t

<400> SEQUENCE: 5
gngggagtat ctgagtccag 20

<210> SEQ ID NO 6
<211> LENGTH: 20
<212> TYPE: DNA
<213> ORGANISM: Unknown
<220> FEATURE:
<223> OTHER INFORMATION: Synthesized

<400> SEQUENCE: 6
gttggagcct ctgagtccag 20

<210> SEQ ID NO 7
<211> LENGTH: 20
<212> TYPE: DNA
<213> ORGANISM: Unknown
<220> FEATURE:
<223> OTHER INFORMATION: Synthesized

<400> SEQUENCE: 7
ggaggaacat ctgagtccag 20

<210> SEQ ID NO 8
<211> LENGTH: 20
<212> TYPE: DNA
<213> ORGANISM: Unknown
<220> FEATURE:
<223> OTHER INFORMATION: Synthesized

<400> SEQUENCE: 8
ggaggagcac ctgagtccag 20

<210> SEQ ID NO 9
<211> LENGTH: 20

<212> TYPE: DNA
<213> ORGANISM: Unknown
<220> FEATURE:
<223> OTHER INFORMATION: Synthesized

<400> SEQUENCE: 9
gatggtgcat ctgactccag 20

<210> SEQ ID NO 10
<211> LENGTH: 20
<212> TYPE: DNA
<213> ORGANISM: Unknown
<220> FEATURE:
<223> OTHER INFORMATION: Synthesized

<400> SEQUENCE: 10
attggagcct ctgagtccag 20

<210> SEQ ID NO 11
<211> LENGTH: 21
<212> TYPE: DNA
<213> ORGANISM: Unknown
<220> FEATURE:
<223> OTHER INFORMATION: Synthesized

<400> SEQUENCE: 11
gtgtggagta tccgagtcca g 21

<210> SEQ ID NO 12
<211> LENGTH: 21
<212> TYPE: DNA
<213> ORGANISM: Unknown
<220> FEATURE:
<223> OTHER INFORMATION: Synthesized

<400> SEQUENCE: 12
gataggaaca tctgagacca g 21

<210> SEQ ID NO 13
<211> LENGTH: 20
<212> TYPE: DNA
<213> ORGANISM: Unknown
<220> FEATURE:
<223> OTHER INFORMATION: Synthesized

<400> SEQUENCE: 13
gatggagctt ctgagtcctg 20

<210> SEQ ID NO 14
<211> LENGTH: 20
<212> TYPE: DNA
<213> ORGANISM: Unknown
<220> FEATURE:
<223> OTHER INFORMATION: Synthesized

<400> SEQUENCE: 14
gaaggatcat ctgagtccag 20

<210> SEQ ID NO 15
<211> LENGTH: 23
<212> TYPE: DNA
<213> ORGANISM: Unknown
<220> FEATURE:
<223> OTHER INFORMATION: Synthesized

<400> SEQUENCE: 15

```
ggtgaagagc atctggagtc cag                                             23


<210> SEQ ID NO 16
<211> LENGTH: 20
<212> TYPE: DNA
<213> ORGANISM: Unknown
<220> FEATURE:
<223> OTHER INFORMATION: Synthesized

<400> SEQUENCE: 16

gtaggagtat ctgagtccag                                                 20


<210> SEQ ID NO 17
<211> LENGTH: 20
<212> TYPE: DNA
<213> ORGANISM: Unknown
<220> FEATURE:
<223> OTHER INFORMATION: Synthesized

<400> SEQUENCE: 17

gctggagaaa ctgagtccag                                                 20


<210> SEQ ID NO 18
<211> LENGTH: 19
<212> TYPE: DNA
<213> ORGANISM: Unknown
<220> FEATURE:
<223> OTHER INFORMATION: Synthesized

<400> SEQUENCE: 18

cctggagctc agagtccag                                                  19


<210> SEQ ID NO 19
<211> LENGTH: 20
<212> TYPE: DNA
<213> ORGANISM: Unknown
<220> FEATURE:
<223> OTHER INFORMATION: Synthesized

<400> SEQUENCE: 19

gttggatcat ctgagttcag                                                 20


<210> SEQ ID NO 20
<211> LENGTH: 20
<212> TYPE: DNA
<213> ORGANISM: Unknown
<220> FEATURE:
<223> OTHER INFORMATION: Synthesized

<400> SEQUENCE: 20

gttgaaccat ctgagtccag                                                 20


<210> SEQ ID NO 21
<211> LENGTH: 20
<212> TYPE: DNA
<213> ORGANISM: Unknown
<220> FEATURE:
<223> OTHER INFORMATION: Synthesized

<400> SEQUENCE: 21

gaaggatcac ctgagtccag                                                 20


<210> SEQ ID NO 22
<211> LENGTH: 46
<212> TYPE: DNA
<213> ORGANISM: Unknown
```

```
<220> FEATURE:
<223> OTHER INFORMATION: Synthesized
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t

<400> SEQUENCE: 22

cnangtgttt aattgagttg tcatatgtta ataacggtat cangnc                    46


<210> SEQ ID NO 23
<211> LENGTH: 46
<212> TYPE: DNA
<213> ORGANISM: Unknown
<220> FEATURE:
<223> OTHER INFORMATION: Synthesized
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t

<400> SEQUENCE: 23

gncntgatac cgttattaac atatgacaac tcaattaaac acntng                    46


<210> SEQ ID NO 24
<211> LENGTH: 35
<212> TYPE: DNA
<213> ORGANISM: Unknown
<220> FEATURE:
<223> OTHER INFORMATION: Synthesized

<400> SEQUENCE: 24

cagtgtttaa ttgagttgtc atatgttaat aacgg                                35


<210> SEQ ID NO 25
<211> LENGTH: 31
<212> TYPE: DNA
<213> ORGANISM: Unknown
<220> FEATURE:
<223> OTHER INFORMATION: Synthesized

<400> SEQUENCE: 25

gctgataccg ttattaacat atgacaactc a                                    31
```